(12) United States Patent
Sugita et al.

(10) Patent No.: US 8,226,233 B2
(45) Date of Patent: Jul. 24, 2012

(54) IMAGE ACQUISITION APPARATUS AND IMAGE ACQUISITION METHOD USING OPTICAL COHERENCE TOMOGRAPHY

(75) Inventors: Mitsuro Sugita, Tokyo (JP); Shuichi Kobayashi, Yokohama (JP); Koji Nozato, Yokohama (JP); Akihiro Katayama, Yokohama (JP); Futoshi Hirose, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/101,050

(22) Filed: May 4, 2011

(65) Prior Publication Data

US 2011/0205548 A1     Aug. 25, 2011

Related U.S. Application Data

(63) Continuation of application No. 12/636,508, filed on Dec. 11, 2009, now Pat. No. 7,954,947.

(30) Foreign Application Priority Data

Dec. 26, 2008    (JP) .................................. 2008-332190

(51) Int. Cl.
*A61B 3/14*        (2006.01)

(52) U.S. Cl. ......... 351/206; 351/205; 351/246; 356/496
(58) Field of Classification Search .................. 351/205, 351/206, 210, 221, 246; 356/450, 477, 479, 356/496, 497
See application file for complete search history.

(56) References Cited

U.S. PATENT DOCUMENTS

| | | | |
|---|---|---|---|
| 2006/0132790 A1* | 6/2006 | Gutin | 356/479 |
| 2007/0188707 A1* | 8/2007 | Nanjo | 351/206 |
| 2007/0195269 A1* | 8/2007 | Wei et al. | 351/221 |
| 2009/0027689 A1* | 1/2009 | Yun et al. | 356/511 |

* cited by examiner

*Primary Examiner* — Huy K Mai
(74) *Attorney, Agent, or Firm* — Canon USA Inc IP Division

(57) ABSTRACT

An image acquisition apparatus that uses optical coherence tomography includes a scanning unit provided within a light path that guides signal light to be incident on an examination object towards the examination object and configured to scan the signal light in a main scanning direction; and a control unit configured to control the scanning unit such that an integration time of an optical interference signal per pixel in at least one predetermined area other than opposite ends, in the main scanning direction, of an image acquisition region scanned by a plurality of main scan lines is increased relative to that of an area other than the predetermined area.

16 Claims, 26 Drawing Sheets

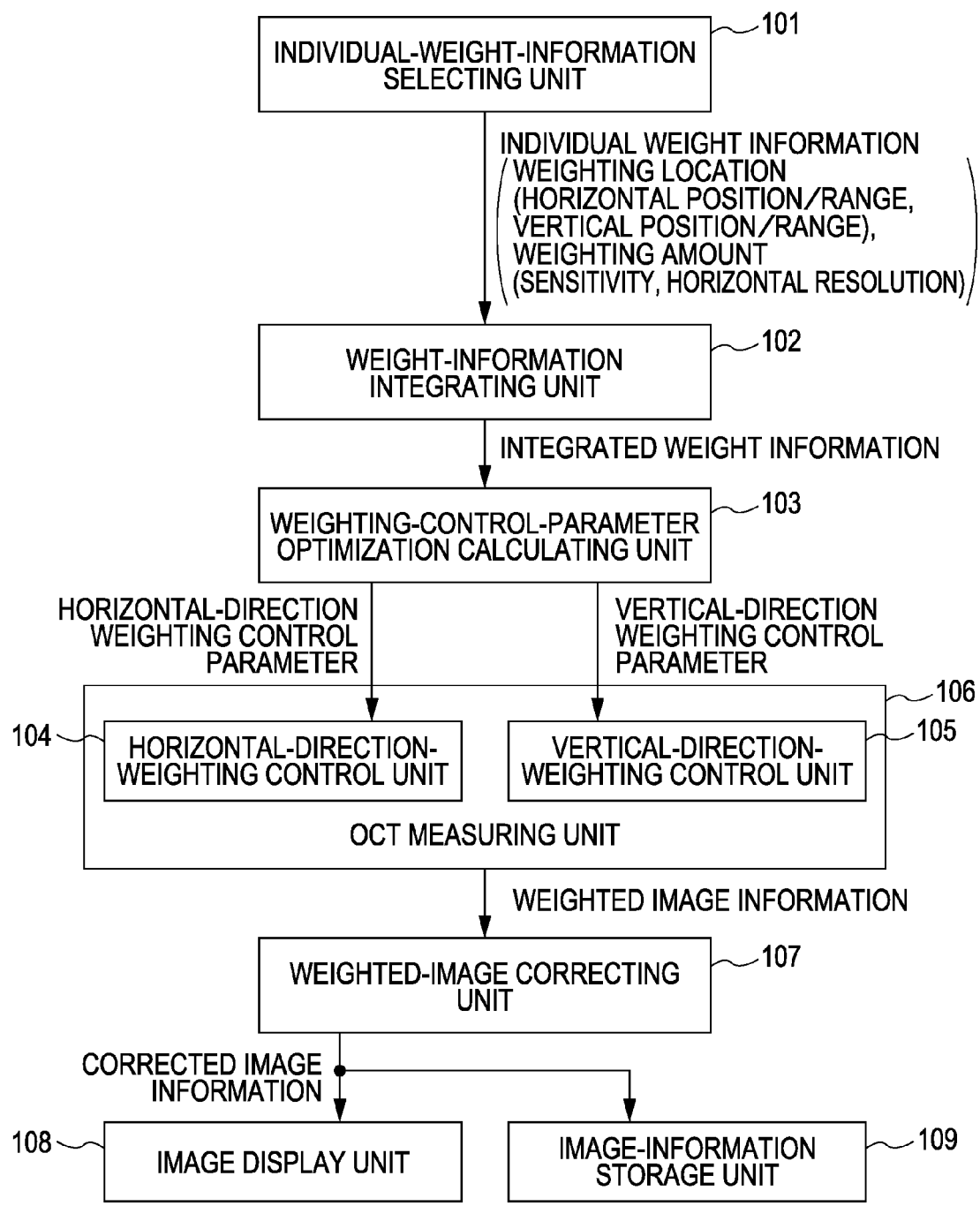

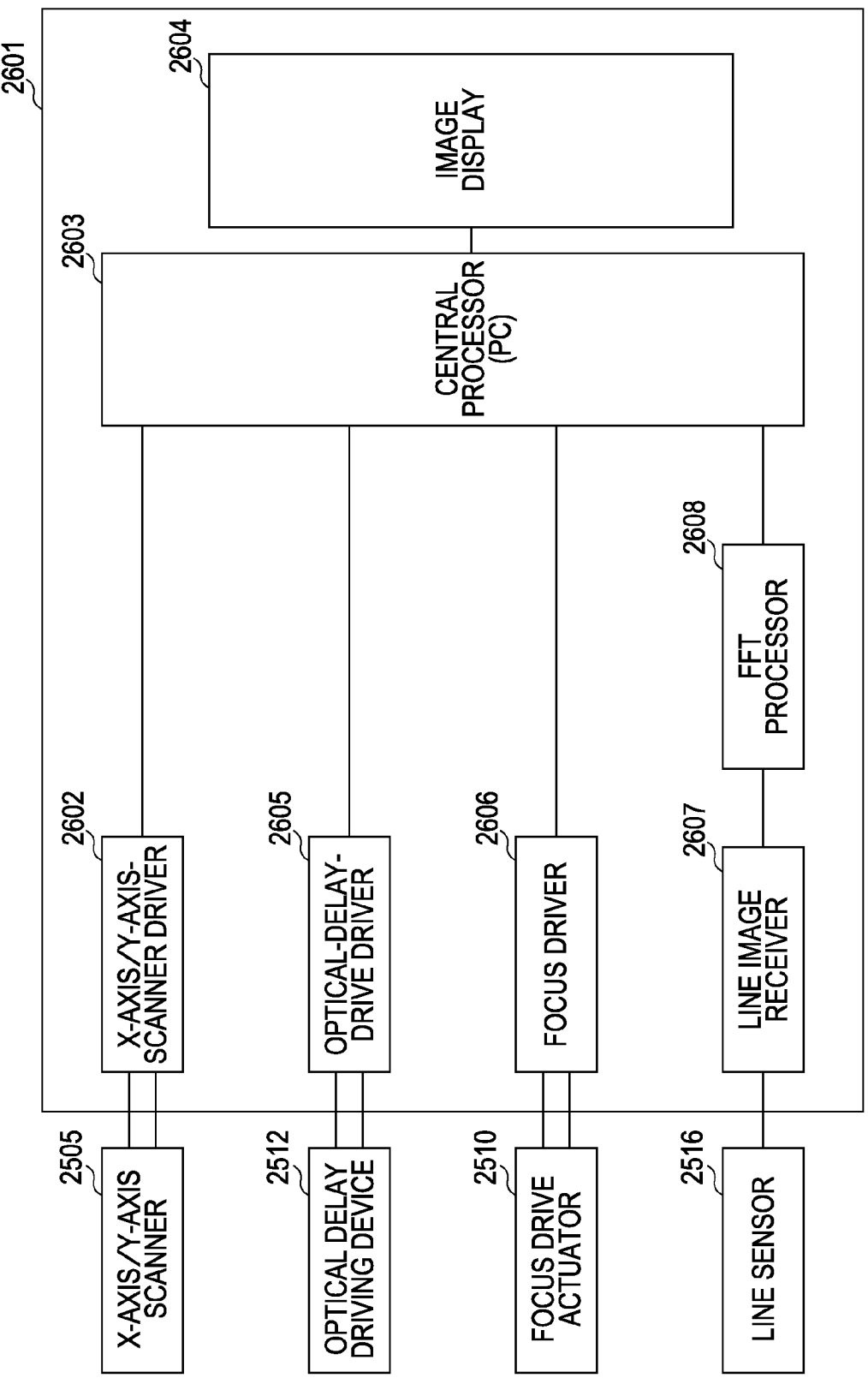

cos(ωt) + 0.3cos(3ωt)

cos(ωt), 0.3cos(3ωt)

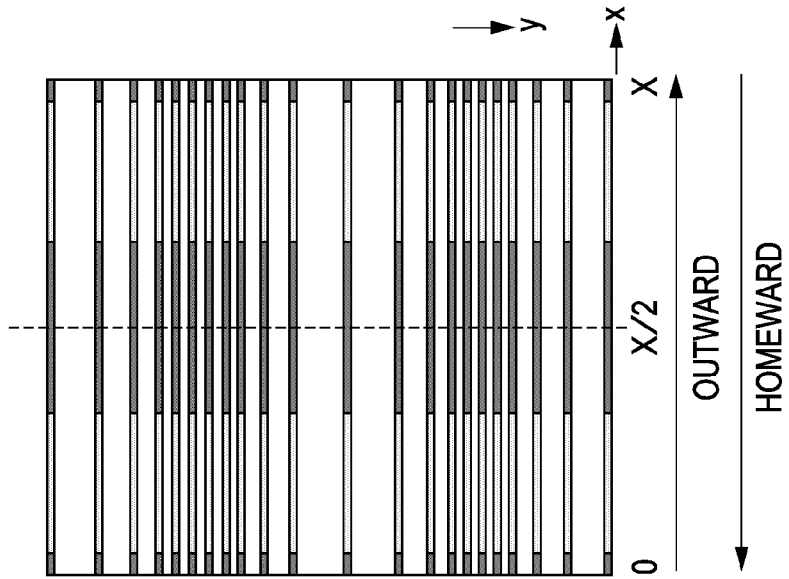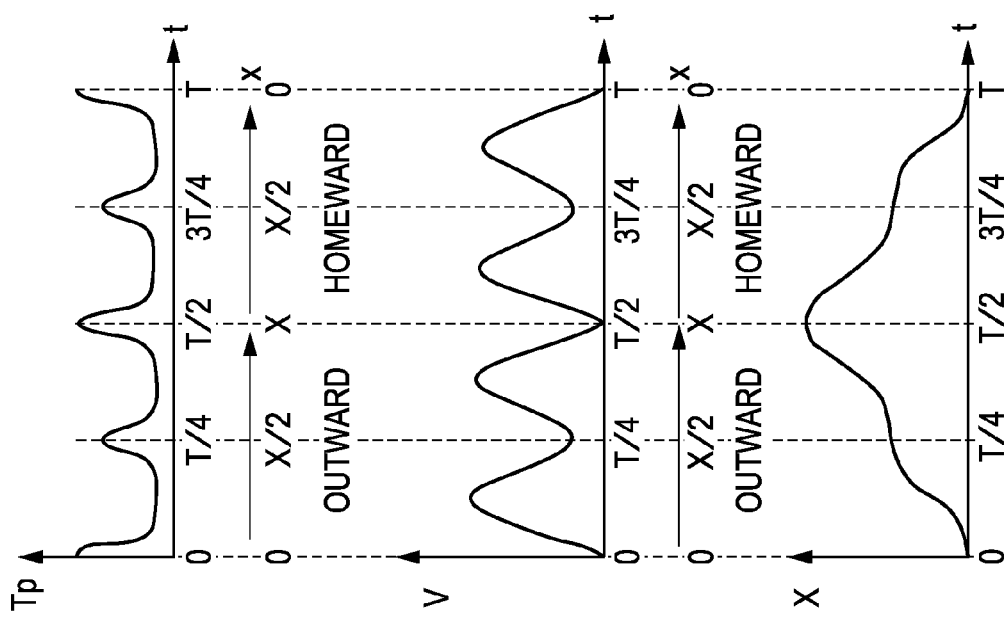

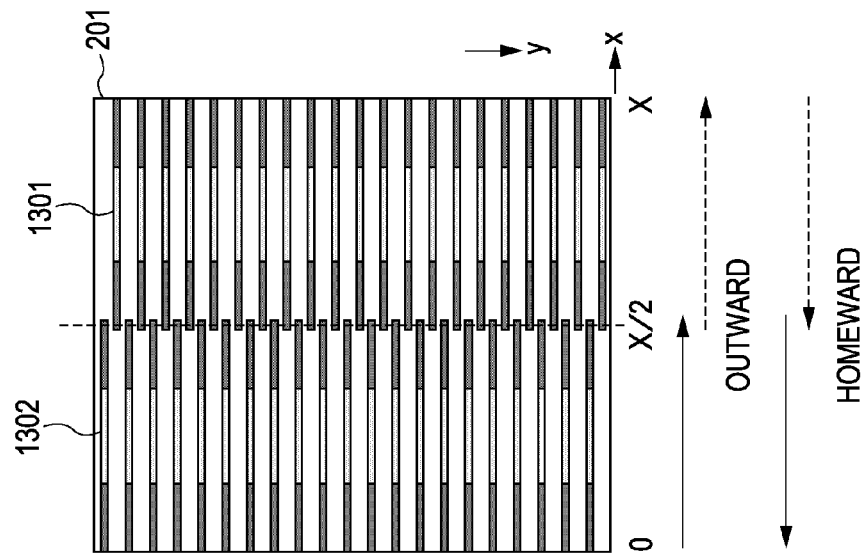
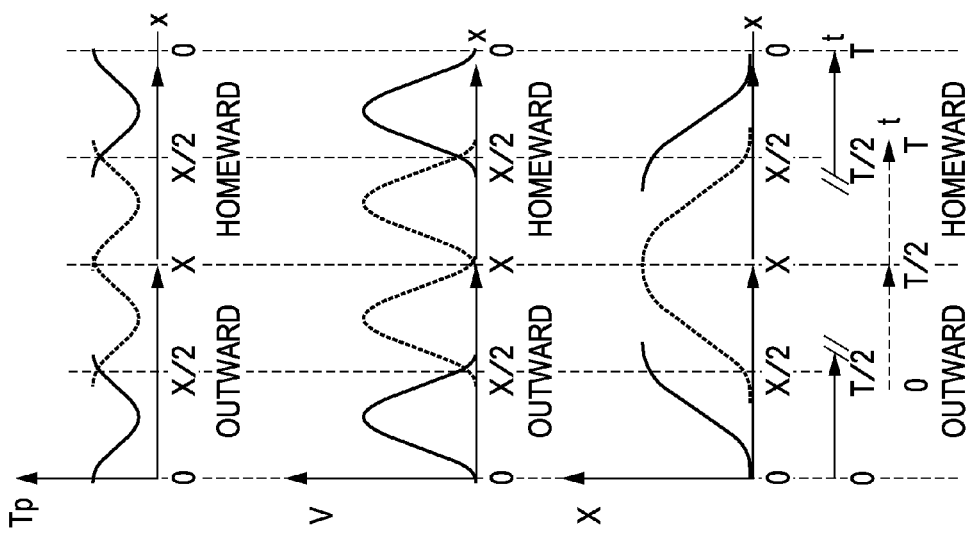

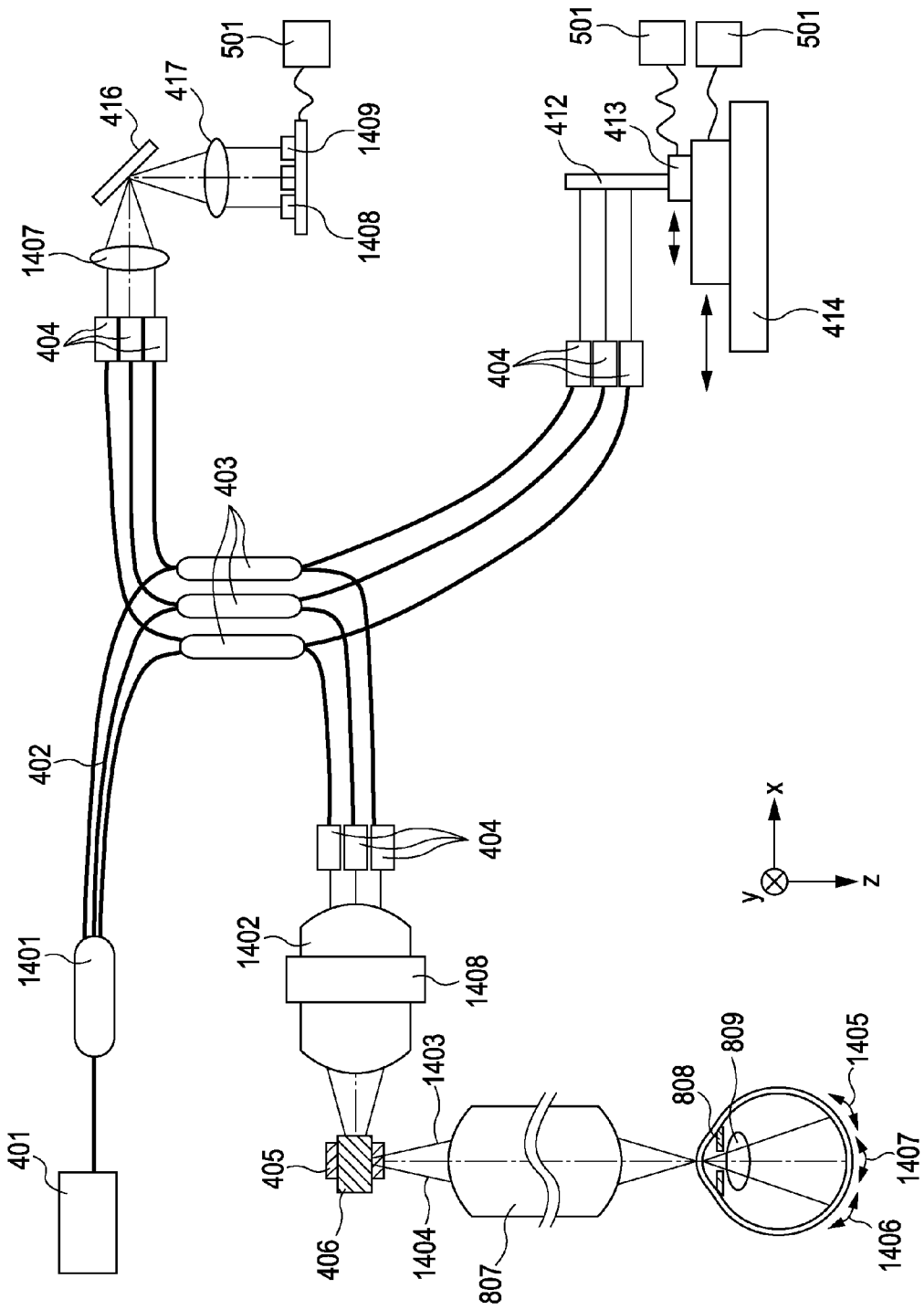

IMAGE ACQUISITION APPARATUS AND IMAGE ACQUISITION METHOD USING OPTICAL COHERENCE TOMOGRAPHY

CROSS REFERENCE TO RELATED APPLICATIONS

This application is a Continuation of U.S. patent application Ser. No. 12/636508, filed Dec. 11, 2009, entitled "IMAGE ACQUISITION APPARATUS AND IMAGE ACQUISITION METHOD USING OPTICAL COHERENCE TOMOGRAPHY", the content of which is expressly incorporated by reference herein in its entirety. This application also claims priority from Japanese Patent Application Nos. 2008-332190, filed Dec. 26, 2008, which is hereby incorporated by reference herein in its entirety.

BACKGROUND OF THE INVENTION

1. Field of the Invention

The present invention relates to image acquisition apparatuses and image acquisition methods that use optical coherence tomography.

2. Description of the Related Art

In recent years, image acquisition apparatuses that use optical coherence tomography (referred to as "OCT" hereinafter) have been used in the ophthalmologic field for acquiring fundus tomographic images.

Accuracy in diagnosis is significantly affected by image distortion (motion artifact) caused by biological motion (eye motion in particular) occurring during a fundus image acquisition operation by OCT. A typical eye motion involves a three-dimensional involuntary eye movement of about 100 μm per second in the planar direction (referred to as "horizontal direction" hereinafter) as well as the depth direction ("referred to as "vertical direction" hereinafter) of a fundus.

OCT mainly includes two methods, namely, time domain OCT (TD-OCT) and Fourier domain OCT (FD-OCT). In TD-OCT, about one second is required for acquiring a tomographic image (a two-dimensional image constituted by a one-dimensional image in the horizontal direction and a one-dimensional image in the vertical direction) by B-scanning. Therefore, in order to acquire about 100 three-dimensional images by B scanning, there is a problem in that the image acquisition takes too much time relative to the eye movement. On the other hand, in FD-OCT, high-speed image acquisition (in which a three-dimensional fundus image can be acquired in about one to three seconds) that is ten times faster than TD-OCT is possible. FD-OCT includes spectral domain OCT (SD-OCT) and swept source OCT (SS-OCT).

Ophthalmologic OCT is desirably applied to screening in group examinations for the purpose of early detection of three major diseases (diabetic retinopathy, glaucoma, and age-related macular degeneration) that can possibly lead to blindness. In group examinations, it is essential to increase the number of examined people per unit time as much as possible. Therefore, it is important to reduce the number of retakes of images. However, in image acquisition using ophthalmologic OCT, if image distortion occurs as a result of eye movement or body movement, the image needs to be retaken again. In addition, since it is necessary to maintain the image quality as much as possible to prevent lowering of diagnostic quality, high-speed image acquisition is desired. Moreover, although collective image acquisition of a wide region including a macula and an optic disk is desired, an increase in an image acquisition region leads to a longer image acquisition time.

In light of this, in image acquisition using OCT, there is a method of efficiently acquiring image information of an area of diagnostic importance by setting the number of scan lines extending in the area of importance greater than that in other areas. FIG. 10C illustrates a grating that allows the center of an OCT image acquisition region 2701 to be scanned more than other regions when an area of importance is located in the center. Each line schematically represents a scan line 2702 that corresponds to a single main scanning process. Furthermore, US Patent Application Publication No. 2007/0195269 discloses a method in which the grating is disposed in a polar coordinate system, the distance between scan lines is adjusted in a radial direction and a tangential direction of a circle, and an area of importance is weighted.

SUMMARY OF THE INVENTION

When the aforementioned scanning method is used, the pixels on each scan line are arranged uniformly on the scan line regardless of whether or not a pixel is located in the area of importance. For this reason, the area of diagnostic importance is not necessarily efficiently weighted, and there is room for improvement in this aspect.

In a method that involves performing scanning by two-dimensionally switching main scanning and sub scanning shown in FIG. 10C, a main scan rate of 1 kHz or higher can be achieved by using a resonant scanner. However, a high-speed resonant scanner cannot be used in either of the two-dimensional axes. The reason for this is, because main scanning and sub scanning are switched in the course of a scanning operation, a non-resonance operation is required during sub scanning. Therefore, the scanning method in FIG. 10C makes high-speed scanning difficult.

As mentioned above, in the image acquisition apparatus using OCT of the related art, it is difficult to efficiently achieve high-speed wide-field-angle image acquisition required in screening in group examinations by weighting the area of importance.

The present invention provides an image acquisition apparatus that uses OCT, which allows for weighting above scan lines with respect to an area of importance that is to become an examined subject of an examination object.

An image acquisition apparatus that uses optical coherence tomography according to an aspect of the present invention is configured to split light from a light source into signal light and reference light, guide the signal light to an examination object and the reference light to a reference mirror, and acquire a tomographic image of the examination object by using return light obtained as a result of the signal light reflected or diffused by the examination object and the reference light reflected by the reference mirror. The image acquisition apparatus includes an optical-scanning control unit provided within a light path that guides the signal light towards the examination object and configured to control optical scanning in a main scanning direction; and a control unit configured to control the optical-scanning control unit by increasing an integration time of an optical interference signal per unit scan-line length in at least one predetermined location other than opposite ends, in the main scanning direction, of a predetermined image acquisition region scanned by a plurality of main scan lines.

An image acquisition apparatus that uses optical coherence tomography according to another aspect of the present invention includes a scanning unit provided within a light path that guides signal light to be incident on an examination object towards the examination object and configured to scan the signal light in a main scanning direction; and a control unit configured to control the scanning unit such that an integration time of an optical interference signal per pixel in at least one predetermined area other than opposite ends, in the main scanning direction, of an image acquisition region scanned by a plurality of main scan lines is increased relative to that of an area other than the predetermined area.

An image acquisition method using optical coherence tomography according to an aspect of the present invention includes splitting light from a light source into signal light and reference light and guiding the signal light to an examination object and the reference light to a reference mirror; acquiring a tomographic image of the examination object by using return light obtained as a result of the signal light reflected or diffused by the examination object and the reference light reflected by the reference mirror; and controlling an optical scanning operation in a main scanning direction by increasing an integration time of an optical interference signal per unit scan-line length in at least one predetermined location other than opposite ends, in the main scanning direction, of a predetermined image acquisition region scanned by a plurality of main scan lines.

According to the present invention, the image acquisition apparatus that uses OCT to acquire a tomographic image allows for weighting above scan lines with respect to an area of importance that is to become an examined subject of an examination object.

Further features of the present invention will become apparent from the following description of exemplary embodiments with reference to the attached drawings.

BRIEF DESCRIPTION OF THE DRAWINGS

FIGS. 1A to 1E schematically illustrate the function of an image acquisition apparatus according to an embodiment of the present invention.

FIG. 4A is a block diagram showing the function of a control/signal-processing unit according to an embodiment of the present invention and FIG. 4B is a block diagram showing the function of a control/signal-processing unit of related art.

FIGS. 9A to 9C schematically illustrate an image acquisition apparatus according to an embodiment of the present invention.

DESCRIPTION OF THE EMBODIMENTS

Figure 1B:
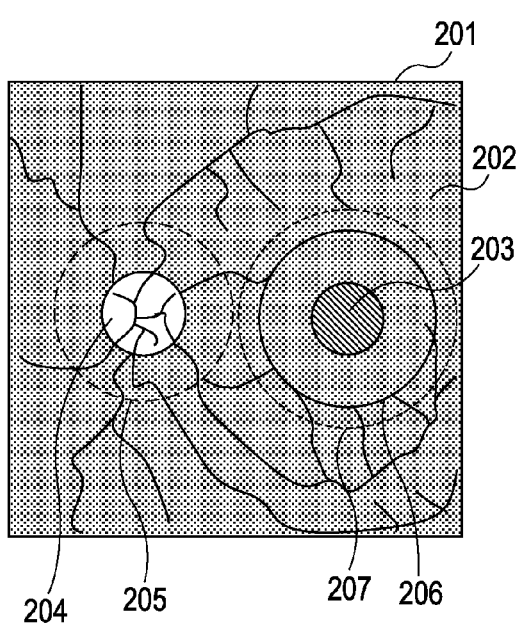

Embodiments of the present invention will be described below with reference to the drawings.

First Embodiment

An image acquisition apparatus according to a first embodiment of the present invention for acquiring a tomographic image of an examination object by OCT is as follows.

The image acquisition apparatus includes a scanning unit disposed in a light path that guides signal light to be incident on the examination object towards the examination object. Specifically, the scanning unit is for scanning the signal light in the main scanning direction.

The image acquisition apparatus also includes a control unit configured to control the scanning unit such that the integration time of an optical interference signal per pixel in at least one predetermined area other than opposite ends, in the main scanning direction, of an image acquisition region scanned by a plurality of main scan lines is increased relative to that of areas other than the predetermined area.

The image acquisition apparatus that uses OCT (simply referred to as "OCT image acquisition apparatus" hereinafter) generally has the following configuration.

First, light emitted from a light source is split into signal light and reference light, and the signal light and the reference light are respectively guided to the examination object and a reference mirror. Then, using return light obtained as a result of the signal light reflected or diffused by the examination object and the reference light reflected by the reference mirror, the image acquisition apparatus acquires a tomographic image of the examination object.

The scanning unit according to this embodiment may alternatively be an optical-scanning control unit disposed in the light path that guides the signal light to the examination object and configured to control optical scanning in the main scanning direction.

The control unit according to this embodiment may alternatively be configured to perform control so as to increase the integration time of an optical interference signal per unit scan-line length in at least one predetermined location other than opposite ends, in the main scanning direction, of a predetermined image acquisition region scanned by a plurality of main scan lines.

The overall function of the OCT image acquisition apparatus according to this embodiment will now be described with reference to a block diagram shown in FIG. 1A. The OCT image acquisition apparatus includes an individual-weighting-information designation unit 101, a weighting-information integrating unit 102, a weighting-control-parameter optimization calculating unit 103, a horizontal-direction-weighting control unit 104, a vertical-direction-weighting control unit 105, an OCT measuring unit 106, a weighted-image correcting unit 107, an image display unit 108, and an image-information storage unit 109.

In three-dimensional image acquisition, the individual-weighting-information designation unit 101 selects an area of importance and the type thereof, depending on the disease being examined within a three-dimensional acquisition range.

Individual weighting information to be selected includes three-dimensional position and range (weighting location) as well as weighting amount of transverse resolution and sensitivity corresponding to the aforementioned position and range.

The weighting-information integrating unit 102 then integrates the individually selected weighting information and sends the integrated weighting information to the weighting-control-parameter optimization calculating unit 103.

A weighting control parameter is a control parameter related to a plurality of controllers included in an OCT device according to the present invention and is optimized on the basis of the integrated weighting information.

The optimized control parameter is separated into control parameters for the horizontal direction and the vertical direction, which are subsequently sent to the horizontal-direction-weighting control unit 104 and the vertical-direction-weighting control unit 105.

The OCT measuring unit 106 that includes the weighting control units performs control to acquire an image, and then outputs the weighted image.

The weighted image information is sent to the weighted-image correcting unit 107 where an alternation in the image caused by the weighting is corrected if necessary.

Examples of an alternation in an image include a change in brightness or vertical positional deviation of an image. The corrected image is sent to the image display unit 108 and the image-information storage unit 109 where image display and data storage are performed.

This embodiment allows for an OCT image acquisition method that includes controlling optical scanning in the main scanning direction by increasing the integration time of an optical interference signal per unit scan-line length in at least one predetermined location other than opposite ends, in the main scanning direction, of a predetermined image acquisition region scanned by a plurality of main scan lines.

An example of weighting selection will now be described in detail.

FIGS. 1B, 1C, 1D, and 1E schematically illustrate how an area of importance is selected in the OCT image acquisition apparatus according to this embodiment.

Figure 1D:
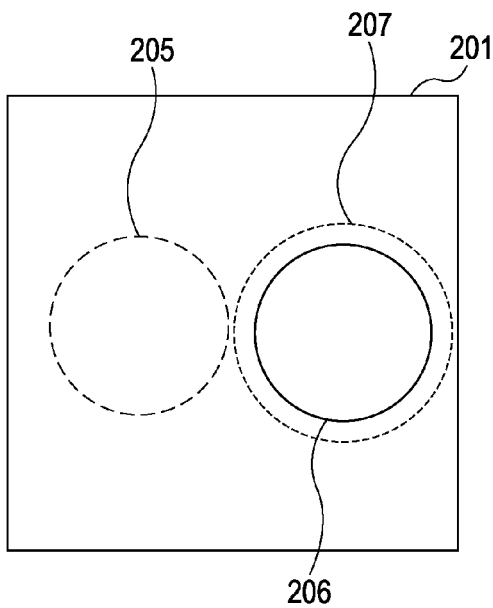
Figure 1C:
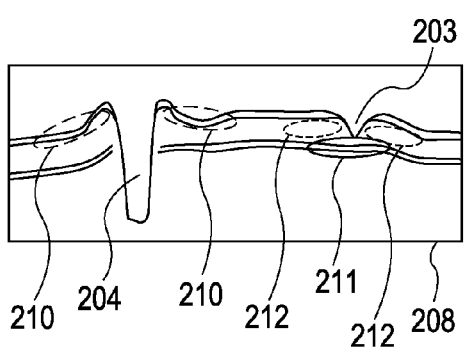

Specifically, FIG. 1B is a top view showing a region of an image to be acquired in the horizontal direction and the vertical direction, and FIG. 1C is a side view thereof, and both of these views are displayed on a display unit. The field angle in this case is about 45°. An image acquisition region 201 includes an image profile 202 of a fundus, which is an examination object, as well as an optic disk 204 and a macula 203, which are characteristic sections.

In screening in group examinations, which is an objective of the invention, glaucoma, age-related macular degeneration, and diabetic retinopathy, which are three major diseases that can possibly lead to blindness, are the most important subjects. Therefore, this embodiment is directed to these diseases.

As shown in FIG. 1B, areas of diagnostic importance regarding these diseases are selected as a selected glaucoma-related important area 205, a selected age-related-macular-degeneration-related important area 206, and a selected diabetic-retinopathy-related important area 207. In this embodiment, these areas are plotted out and selected by a user with graphical user interface (GUI).

Similarly, as shown in FIG. 1C, a selected glaucoma-related important area 210, a selected age-related-macular-degeneration-related important area 211, and a selected diabetic-retinopathy-related important area 212 are selected within a vertical-direction image acquisition region 208.

Figure 1E:
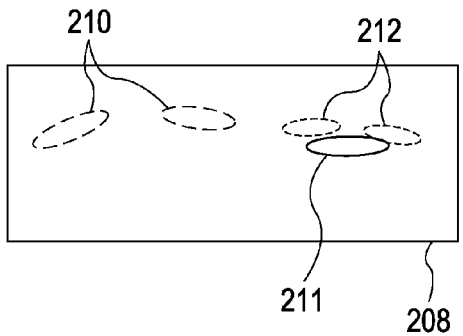

FIGS. 1D and 1E illustrate only the selected weighting information corresponding to the horizontal direction and the vertical direction, respectively. Specifically, weighted sections and the types thereof are displayed as information in FIGS. 1D and 1E. Although the pieces of weighting information are integrated as described above and the actual control parameters are optimized, glaucoma, age-related macular degeneration, and diabetic retinopathy are all weighted with respect to sensitivity in the horizontal direction in this embodiment, and the integration time per pixel is a control parameter. On the other hand, in the vertical direction, a glaucoma-related important area is weighted with respect to both sensitivity and transverse resolution, whereas an age-related-macular-degeneration-related important area and a diabetic-retinopathy-related important area, which are close to each other, are weighted respectively with respect to transverse resolution and sensitivity. This optimization is performed, for example, by using information indicating that an age-related-macular-degeneration-related important area is near the retinal pigment epithelium layer, has a relatively high signal level, and requires transverse resolution for viewing, for example, defects in a photoreceptor cell layer in detail, and also by using information indicating that a diabetic-retinopathy-related important area has a relatively low signal level within a fundus. These pieces of information are appropriately preset and held by the weighting-control-parameter optimization calculating unit 103 and can also be added by, for example, input operation by a user.

Figure 2A:
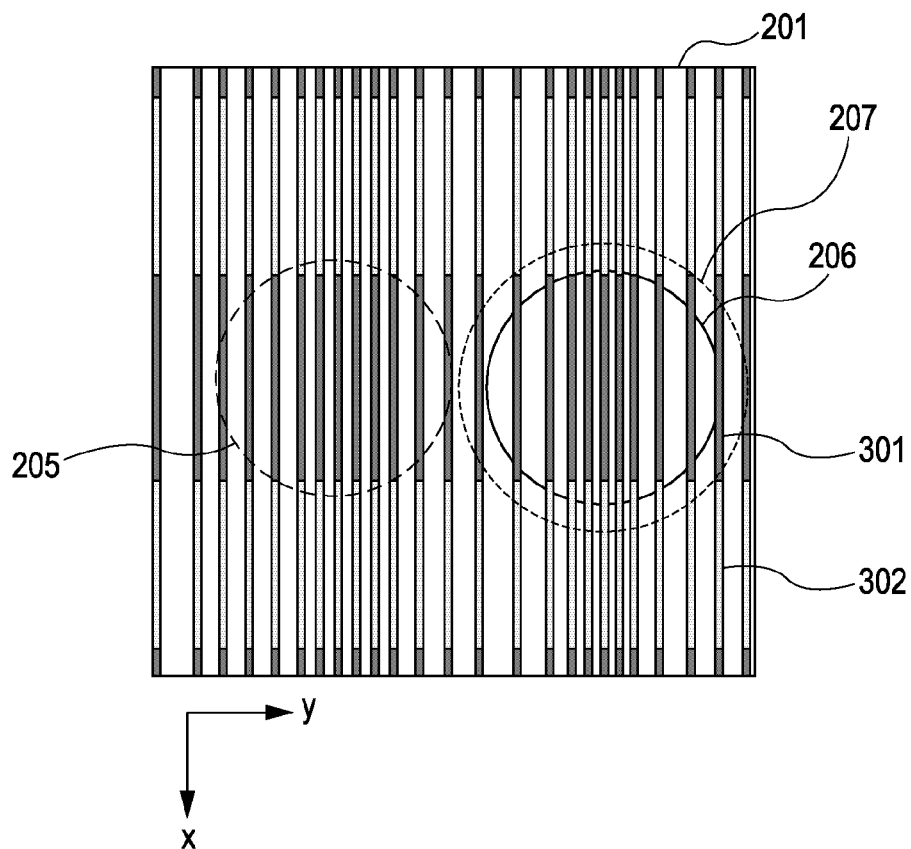
FIGS. 2A to 2F schematically illustrate how weighting control is performed on areas of importance in an embodiment of the present invention.
Figure 2B:
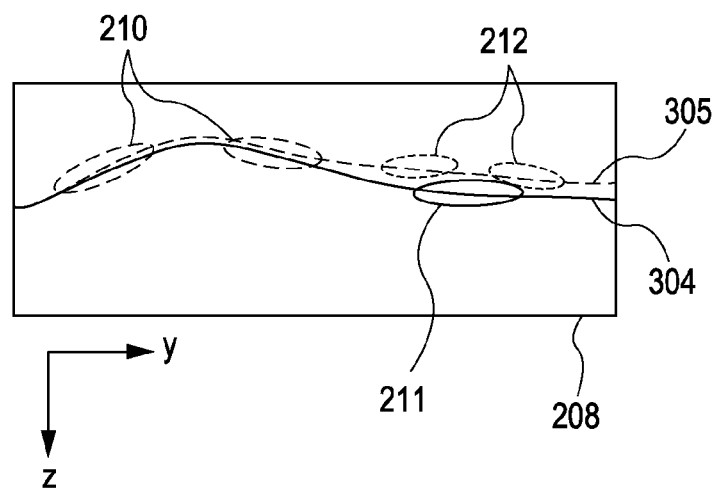

The actual control parameters, the control unit, and the OCT image acquisition apparatus according to this embodiment will now be described. FIGS. 2A and 2B schematically illustrate how weighting control is performed on areas of importance in this embodiment. FIGS. 2A and 2B are diagrams in which profiles related to the control parameters have been added to FIGS. 1D and 1E. FIG. 2A schematically illustrates the state of scan lines. Regarding the scan lines, a midsection 301 of each scan line in the main scanning direction (x-axis) is given a longer integration time per pixel as compared to peripheral sections 302, and this difference in integration time per pixel is roughly expressed by color gradation. In the sub scanning direction (y-axis), the scan lines are arranged such that the density thereof is nonuniform. The areas of importance selected in the main scanning direction and the sub scanning direction are weighted. Referring to FIG. 2B, two control parameters with independent degree of freedom, i.e., a focus position 304 and a zero-delay position 305, are controlled so that they are both made to pass through an area of importance 210 as a glaucoma-related important area. On the other hand, with regard to an age-related-macular-degeneration-related important area and a diabetic-retinopathy-related important area, control operation that causes the former (denoted by 211 in FIG. 2B) and the latter (denoted by 212 in FIG. 2B) to pass through different vertical positions (depth positions in z-axis direction) is performed so that the focus position is made to pass through the important area 211 and the zero-delay position is made to pass through the important area 212.

A detailed configuration of the image acquisition apparatus according to this embodiment, including control modes of focus-position control and zero-delay-position control, will now be described.

Figure 3A:
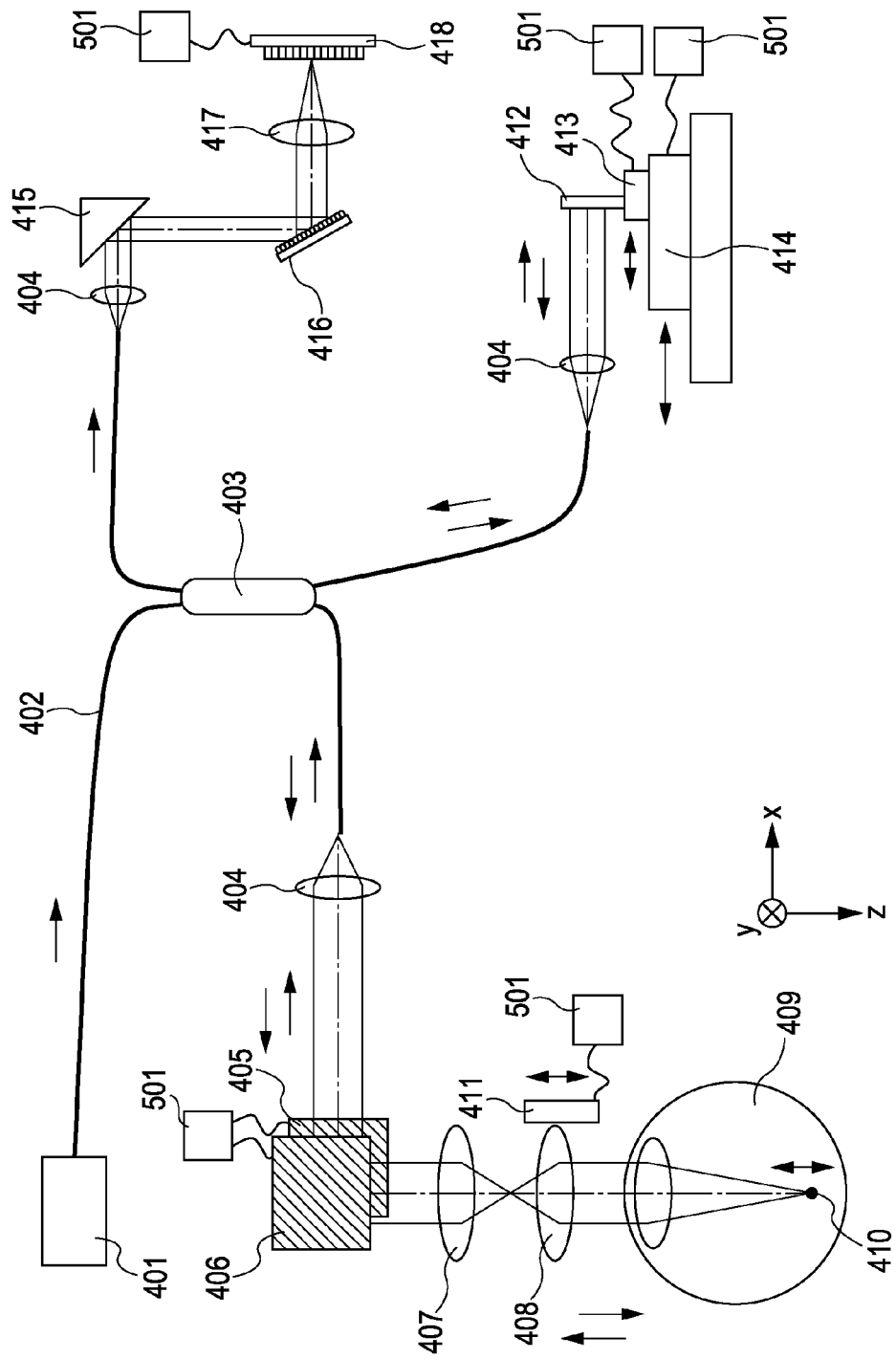
FIGS. 3A to 3C schematically illustrate the configuration of an optical measuring system according to an embodiment of the present invention.

FIG. 3A schematically illustrates the configuration of an optical measurement system of an optical coherence measuring apparatus according to this embodiment. Specifically, light emitted from a light source 401 is optically guided by a single-mode optical fiber 402 so as to enter a fiber optical coupler 403. The fiber optical coupler 403 is a so-called 2×2 type and distributes the light received through the fiber 402 to two output fibers. One of the output fibers is connected to a human-fundus image acquisition optical system acting as a signal light path of a Michelson interferometer, whereas the other output fiber is connected to a reference light path of an interferometer. In the signal light path, the light emitted from the fiber terminal is converted to collimated light by a collimator lens 404 and then propagates through space so as to enter an x-axis scanner 405 and then to a y-axis scanner 406. Both scanners are reflective optical scanning devices that perform one-dimensional reflective angle control and can be combined to perform two-dimensional reflective angle control. The reflected signal light is optically guided by a scan lens 407 and an ocular lens 408 so as to enter a human eye 409. Through the scanning optical system constituted by the x-axis scanner 405, the y-axis scanner 406, the scan lens 407, and the ocular lens 408, the signal light, which is collimated light and receiving an optical effect of the eye, is focused onto a fundus observation area 410 and is two-dimensionally scanned over a surface on the fundus substantially orthogonal to the light axis. The ocular lens 408 adjusts the focus position in the depth direction. The scan control and the focus control are collectively performed together with other control by a control/signal-processing unit 501 connected to the x-axis scanner 405, the y-axis scanner 406, and a focus drive actuator 411. The focus control corresponds to the focus-position control shown in FIG. 2B mentioned above and is performed in synchronization with the scan system so that the focus position is made to pass through an area of importance related to transverse resolution. Of the reflected light and rearward diffused light from the fundus observation area 410, the signal light passing through substantially the same light path and travelling in the reverse direction returns to the fiber optical coupler 403 via the collimator lens 404.

On the other hand, the reference light split via the fiber optical coupler 403 is converted to collimated light by a collimator lens 404 and is reflected by a reference-light mirror 412 disposed on an optical delay-position high-speed fine driving device 413 and an optical delay-position global low-speed driving device 414 so that the light travels reversely through the light path.

The position of the reference-light mirror 412 is controlled by controlling the optical delay-position global low-speed driving device 414 and the optical delay-position high-speed fine driving device 413 so that the total light-path length of the reference light path is globally and finely adjusted to a predetermined length relative to the length of the signal light path.

The delay-position driving devices are each connected to the control/signal-processing unit 501 and are collectively controlled together with other control. The reversely-travelling reference light returns to the fiber optical coupler 403 via the collimator lens 404.

The global light-path length control is performed such that the total light-path length of the reference light path is adjusted to a predetermined length, particularly including compensation for axial length that may vary among individuals, on the basis of the signal light path.

The fine and high-speed control by the optical delay-position high-speed fine driving device 413 corresponds to the zero-delay position control shown in FIG. 2B described above and is performed so that the zero-delay position is made to pass through an area of importance where sensitivity is to be increased.

In this case, a zero-delay position is a vertical position on an examination object when the reference light path length and the signal light path length are equal to each other.

In SD-OCT, the sensitivity is at maximum at the zero-delay position and decreases with increasing distance from a delay position.

When a zero-delay position is set inside the examination object in the depth direction, a mirror image is produced by inverse Fourier transform processing.

Therefore, in this embodiment, the reference light path constituting a coherence measurement system is equipped with a phase modulator (not shown) so as to remove mirror images by a so-called full-range complex (FRC) method.

Although the signal light and the reference light returning to the fiber optical coupler 403 are each split into a component that returns to the light source 401 and a component that travels toward a coherent-light receiving system, the signal light and the reference light propagate through the same single-mode fiber, meaning that they are combined and create optical coherence.

The coherent-light receiving system is a spectroscope in this embodiment, and therefore, OCT in this embodiment is SD-OCT.

The coherent light is converted to collimated light by a collimator lens 404 and is guided to a diffraction grating 416 by a reflective mirror 415. Due to the effect of the diffraction grating 416, the light travels at different angles in accordance with wavelength components of the light including first-order diffraction light.

The wavelength components of the coherent light entering an imaging lens 417 at different angles form images at different positions on a line sensor 418 in accordance with their respective angles.

The image of each wavelength component is read as a light intensity in accordance with each pixel of the line sensor 418, and a signal is sent to the control/signal-processing unit 501.

The configuration and operation of the control/signal-processing unit 501 will now be described.

Figure 4A:
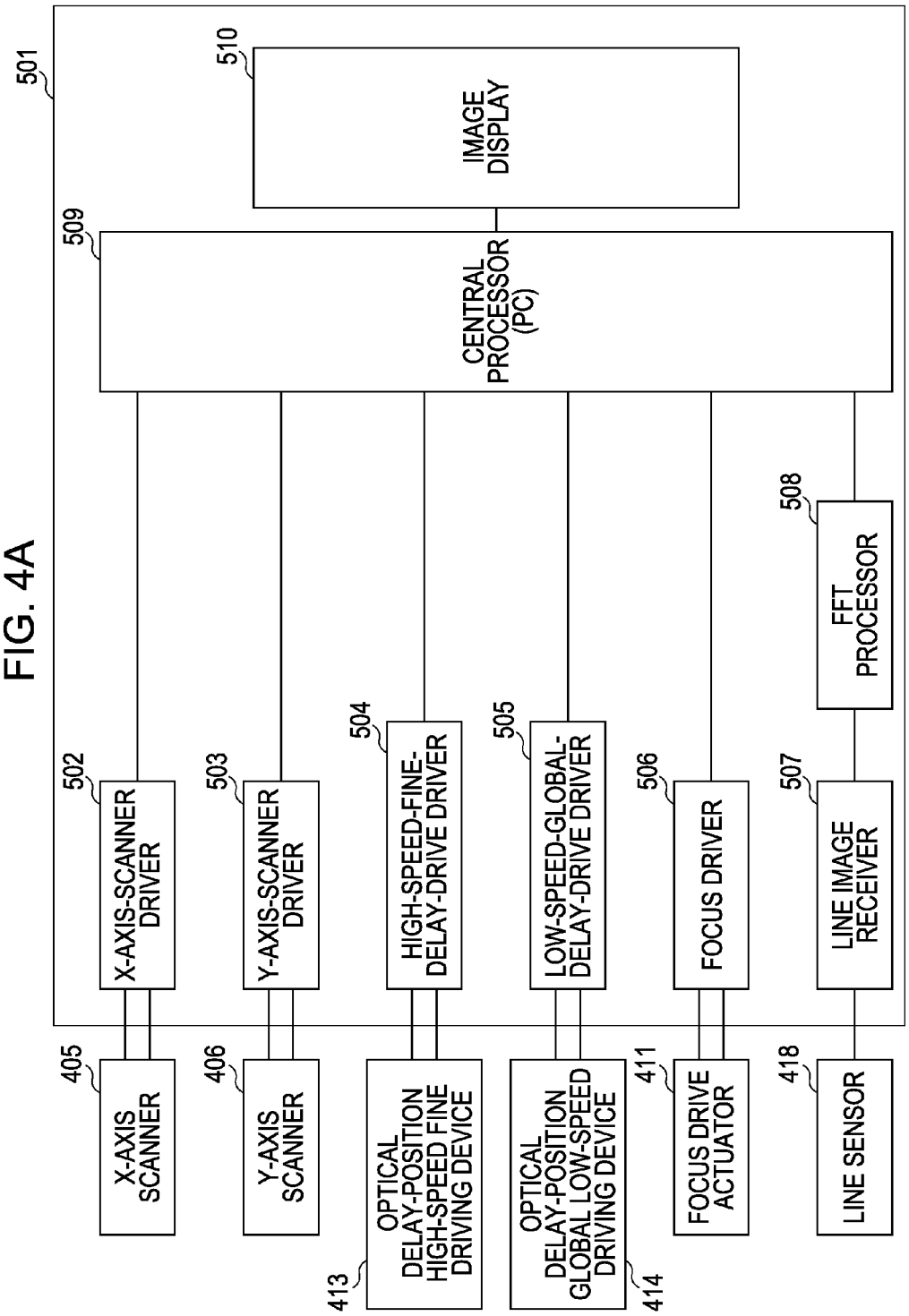

FIG. 4A is a schematic block diagram illustrating the function of the control/signal-processing unit 501 according to this embodiment.

The control/signal-processing unit 501 is configured to control the x-axis scanner 405, the y-axis scanner 406, the optical delay-position global low-speed driving device 414, the optical delay-position high-speed fine driving device 413, the focus drive actuator 411, and the line sensor 418.

On the other hand, the control/signal-processing unit 501 is equipped with drivers and a receiver that are configured to receive angle detection signals, position detection signals, and optical-signal detection signals.

Specifically, a line image receiver 507 receives a group of light intensity signals from the line sensor 418, and a fast Fourier transform (FFT) processor 508 performs inverse Fourier transform processing at high speed on the light intensity signal group. The resultant signal group is sent to a central processor 509.

The central processor 509 receives digital optical-interference signals, having undergone inverse Fourier transform processing, in a time-series fashion and compares each signal with a scanner-position-signal/synchronization-signal from an x-axis-scanner driver 502 and a y-axis-scanner driver 503, a delay-position-signal/synchronization-signal from a high-speed-fine-delay-drive driver 504 and a low-speed-global-delay-drive driver 505, and a focus-position signal from a focus driver 506 so as to match the relationships between the optical interference signals and the positions in the fundus observation area 410. Subsequently, the optical interference signals are allocated to predetermined pixels and formed into images, which are then displayed on an image display 510.

The following is a collective description of the control performed for weighting in this embodiment.

First, the weighting operation in the horizontal direction will be described with reference to the scan control shown in FIG. 2A.

The arrangement of the scan lines in high and low densities is implemented in a similar manner to the related art by controlling the y-axis scanner 406, which is configured to perform sub scanning, shown in FIG. 3A.

Specifically, sub scanning is performed such that the density of scan lines is increased for areas of importance, whereas the density of scan lines is reduced for other areas. Since sub scanning is performed at lower speed as compared with main scanning, the control can be achieved by slightly modifying the control of the related art.

In contrast, for the control of main scanning, the configuration according to the present invention is used for optimizing the integration time per pixel within a scan line.

Specifically, the midsection, which is in an area of importance within a main scan line, is scanned at a speed that is lower than the scanning speed at the peripheral sections.

Therefore, the present invention can still achieve its function by setting an equal scan distance without having to arrange the scan lines in high and low densities by sub-scanning-direction control (FIG. 2A).

The following description relates to control within main scan lines according to this embodiment.

FIGS. 7A to 7F schematically illustrate how weighting is performed by scan control in this embodiment.

FIG. 7A is a graph showing an integration time Tp per pixel, a scan rate V, and a scan position x with respect to a scan time t and a scan position x.

On the other hand, FIG. 7B illustrates how a scan operation is performed, including outward and homeward processes as well as the scan position x. Although FIG. 7B is basically the same as FIG. 2A, the orientation thereof is rotated by 90° relative to that of FIG. 2A.

In FIG. 7A, reference character T denotes the total time for the outward and homeward scanning processes, that is, one cycle of main scanning operation.

The outward scanning process is from t=0 to T/2, whereas the homeward scanning process is from T/2 to T. The x position is from x=0 to X in the outward scanning process and from x=X back to 0 in the homeward scanning process.

In this embodiment, the rate V on a scan line reflects weighting information as a function V(x) of scan position x.

In consequence, as a function Tp(x) of scan position x, the integration time Tp per pixel is made to increase in the midsection of a scan line, which is in an area of importance.

Specifically, when the scan position x in the outward scanning process and the homeward scanning process is near X/2, the integration time Tp per pixel is three times or more.

In an area where the integration time Tp per pixel is increased, the optical interference signal increases and the signal-to-noise (S/N) ratio thus rises.

The reason for this is, since a normal OCT operation area is where shot noise and thermal noise are limited, the S/N ratio is substantially proportional to the integration time.

In consequence, in order to perform such weighting, the scan position x needs to be driven as a function x(t) of time t, as shown in the lowermost section of FIG. 7A.

Figure 5A:
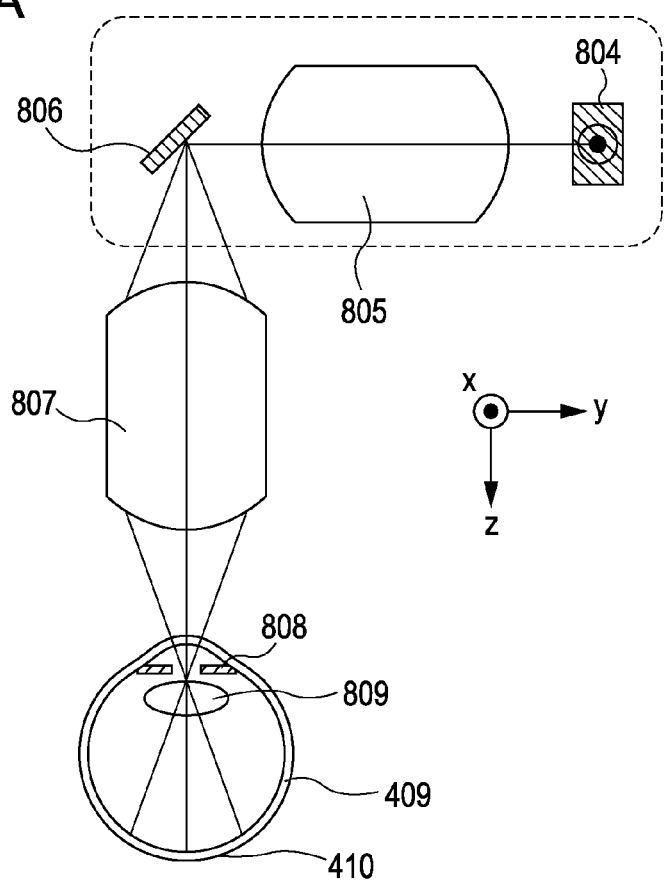
FIGS. 5A to 5G schematically illustrate the configuration of a scanning optical system according to an embodiment of the present invention.
Figure 5B:
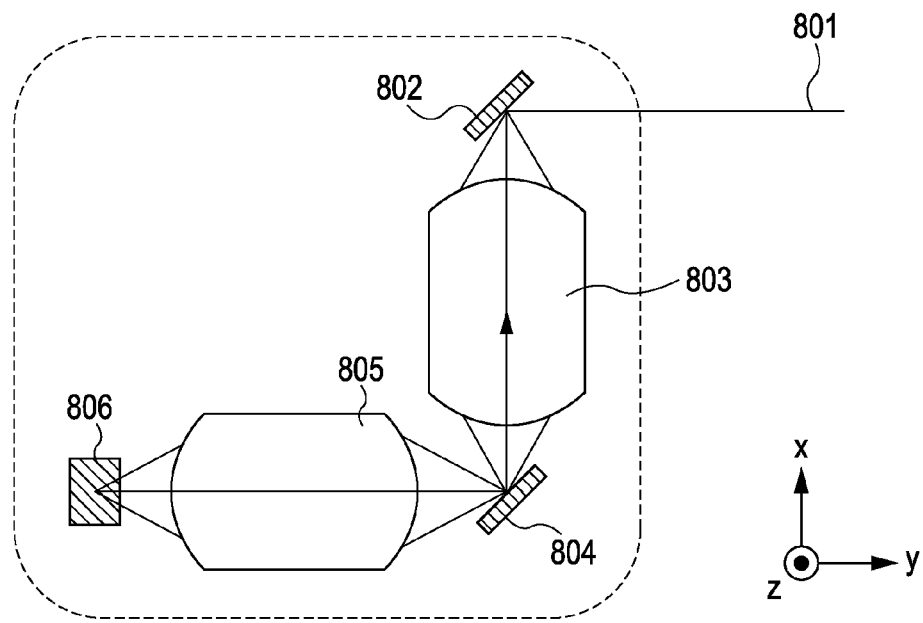

Regarding drive control of the x-axis scanner 405 shown in FIG. 7A, an optical system shown in FIGS. 5A and 5B is used in this embodiment to achieve desired scanning (FIG. 7A) by a combination of main scanning processes.

Specifically, resonance-type x-axis scanners constituted by a first resonant scanner 802 and a second resonant scanner 804 that have two different resonance frequencies are arranged to have an optically conjugate relationship with each other so as to achieve desired scanning (FIG. 7A) by a combination of main scanning processes.

Figure 5C:
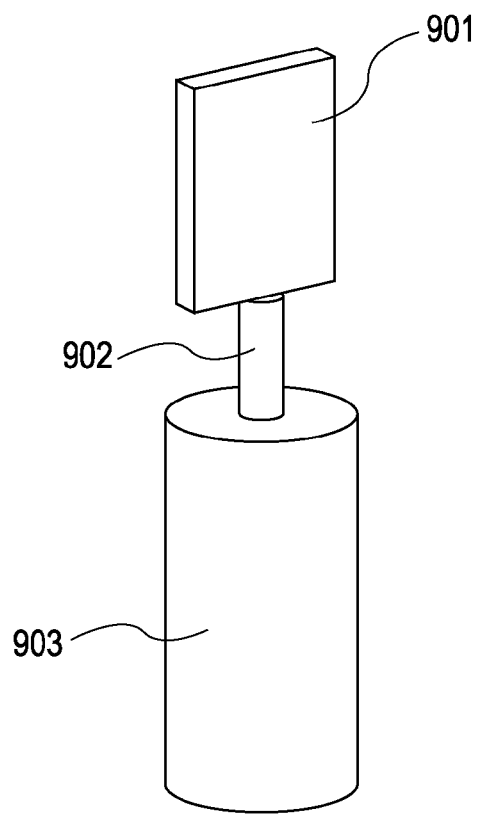
Figure 5D:
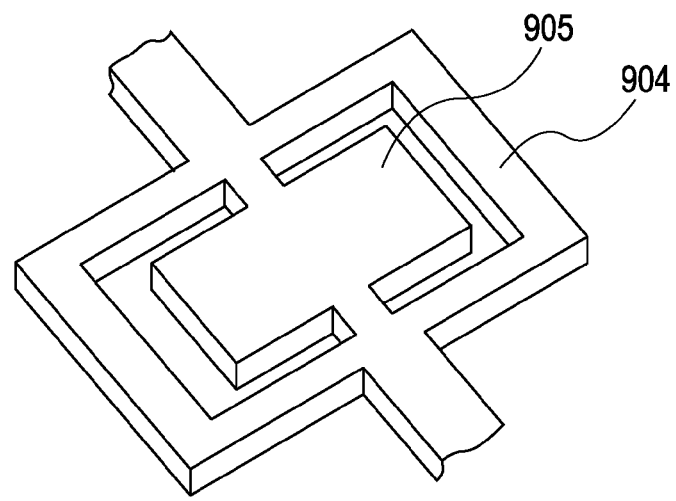

FIGS. 5C and 5D are schematic views of the scanners 802 and 804.

FIGS. 5A and 5B are a top view and a side view, respectively, of an optical system.

In FIG. 5B, signal light 801 enters the first resonant scanner 802. The first resonant scanner 802 and the second resonant scanner 804 are arranged such that the optical-scanning rotational centers of the two have an optically conjugate relationship with each other with respect to a first relay optical system 803. The first and second resonant scanners 802 and 804 have an external appearance as shown in FIG. 5C and each have a rotational mirror 901 configured to perform angular scanning in the form of a trigonometric function having a single predetermined frequency by means of a drive system 903 and a drive shaft 902.

The light reflected by the second resonant scanner 804 is subsequently guided by a second relay optical system 805 towards a y-axis galvano scanner 806, which is configured to perform sub scanning.

The signal light reflected by the y-axis galvano scanner 806 enters the human eye 409 via an ocular optical system 807 and forms an image in a corresponding horizontal position within the fundus in accordance with a two-dimensional scan angle given by the scanners as a result of two main scanning processes and one sub scanning process in addition to an optical effect of the human eye 409.

The resonance frequencies of the first resonant scanner 802 and the second resonant scanner 804 are 2 kHz and 6 kHz, respectively, such that the second resonant scanner 804 is configured to have a resonance frequency three times that of the first resonant scanner 802.

Figure 6A:
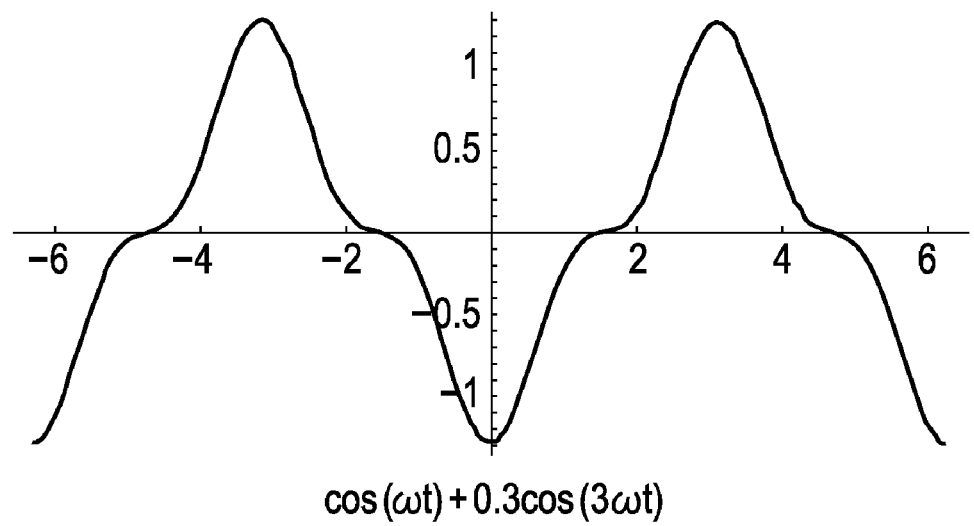
FIGS. 6A to 6I are schematic diagrams for explaining an embodiment of the present invention.
Figure 6B:
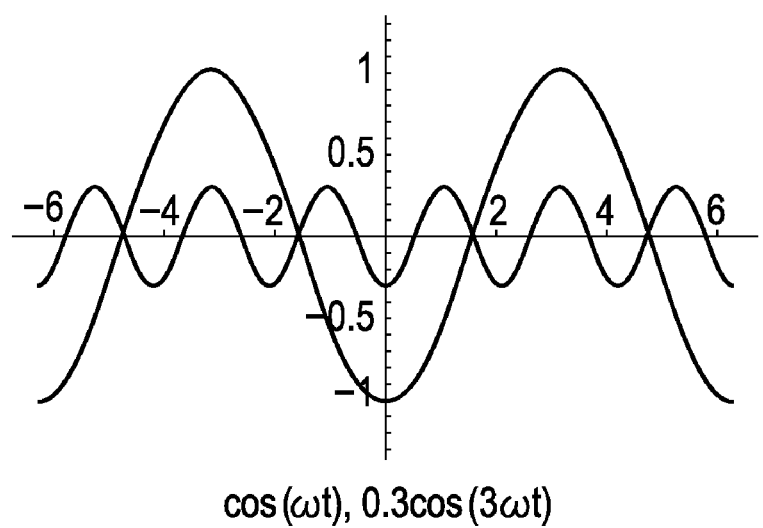

FIGS. 6A and 6B schematically illustrate how scanning is performed by the first and second scanners.

FIG. 6A illustrates combined scanning θ vibration, whereas FIG. 6B illustrates scanning vibrations before they are combined. A combined scan angle is a function θ(t) of time t and can be expressed as follows:

$$\theta(t) = a \cdot \sin(\omega t) + 0.3 a \cdot \sin(3\omega t)$$

where $\omega = 2\pi f$ and $f = 2$ kHz.

Specifically, as shown in FIG. 6B, regarding the phase of scanning vibration of the scanners, a phase difference between the two is 0. Regarding the amplitude, the two have a ratio of 1:0.3. It is apparent from FIG. 6A that the control shown in FIG. 7A, which is a desired scanning operation, can be performed.

In this embodiment, weighting correction includes a mode for correcting the brightness of an area of importance. For example, if a tomographic image is to be formed without any correction in this embodiment, the brightness of an area of importance becomes high in accordance with the integration time per pixel. In light of this, in this mode, the brightness is adjusted in an inversely proportional manner using the rate of integration time.

When the user selects this mode, although the brightness of an area of importance is no different from that when there is no weighting, the acquired image has reduced noise in dark areas, thereby allowing for higher image quality for the area of importance.

According to the first embodiment described above, a scan-type OCT image acquisition apparatus that provides weighted images for multiple kinds of ophthalmological diseases can be achieved.

Second Embodiment

An example including a dual-cycle resonant scanner according to a second embodiment of the present invention will now be described with reference to FIGS. 5D, 5E, and 5F.

In this embodiment, the resonance-type scanning optical systems of the main scanning direction in the first embodiment are changed to a single scanner device.

FIG. 5D schematically illustrates a dual-cycle resonance-type MEMS scanner device used in this embodiment that includes an outer-frame vibrator 904 and a reflective vibrator 905 integrally provided within the outer-frame vibrator 904. The outer-frame vibrator 904 and the reflective vibrator 905 are formed by an MEMS process using a single silicon wafer.

Referring to FIG. 6B, the outer-frame vibrator 904 vibrates at a basic resonance frequency of 2 kHz, whereas the reflective vibrator 905 vibrates at a resonance frequency of 6 kHz, which is three times that of the outer-frame vibrator 904. Thus, a section in the first embodiment where two separate resonant scanners are arranged at predetermined positions via a relay optical system can be replaced by a single scanner. The corresponding configuration according to the second embodiment is shown in FIGS. 5E and 5F.

Figure 5E:
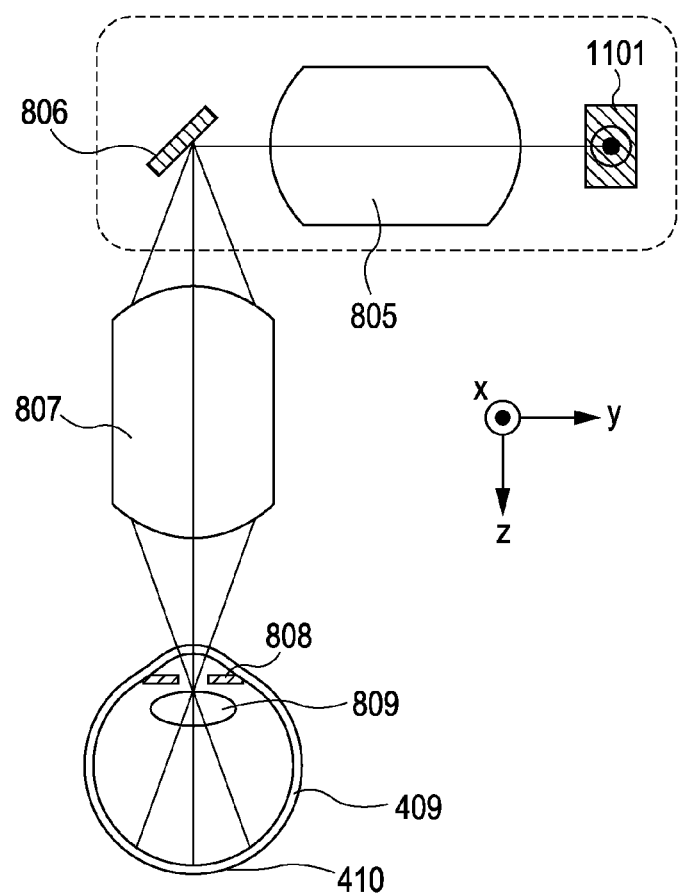
Figure 5F:
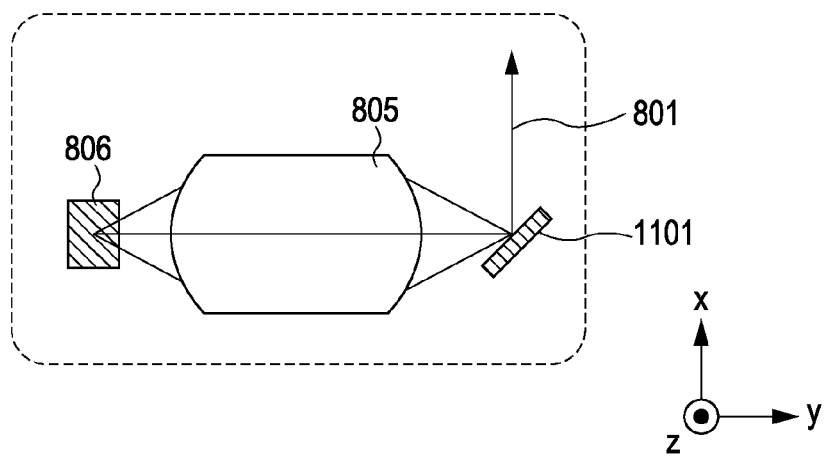

According to this embodiment, with a single reflective surface of an MEMS multi-resonant scanner 1101 shown in FIGS. 5E and 5F, the scanning operation shown in FIG. 7A can substantially be achieved, thereby allowing for size reduction of the optical system.

Figure 5G:
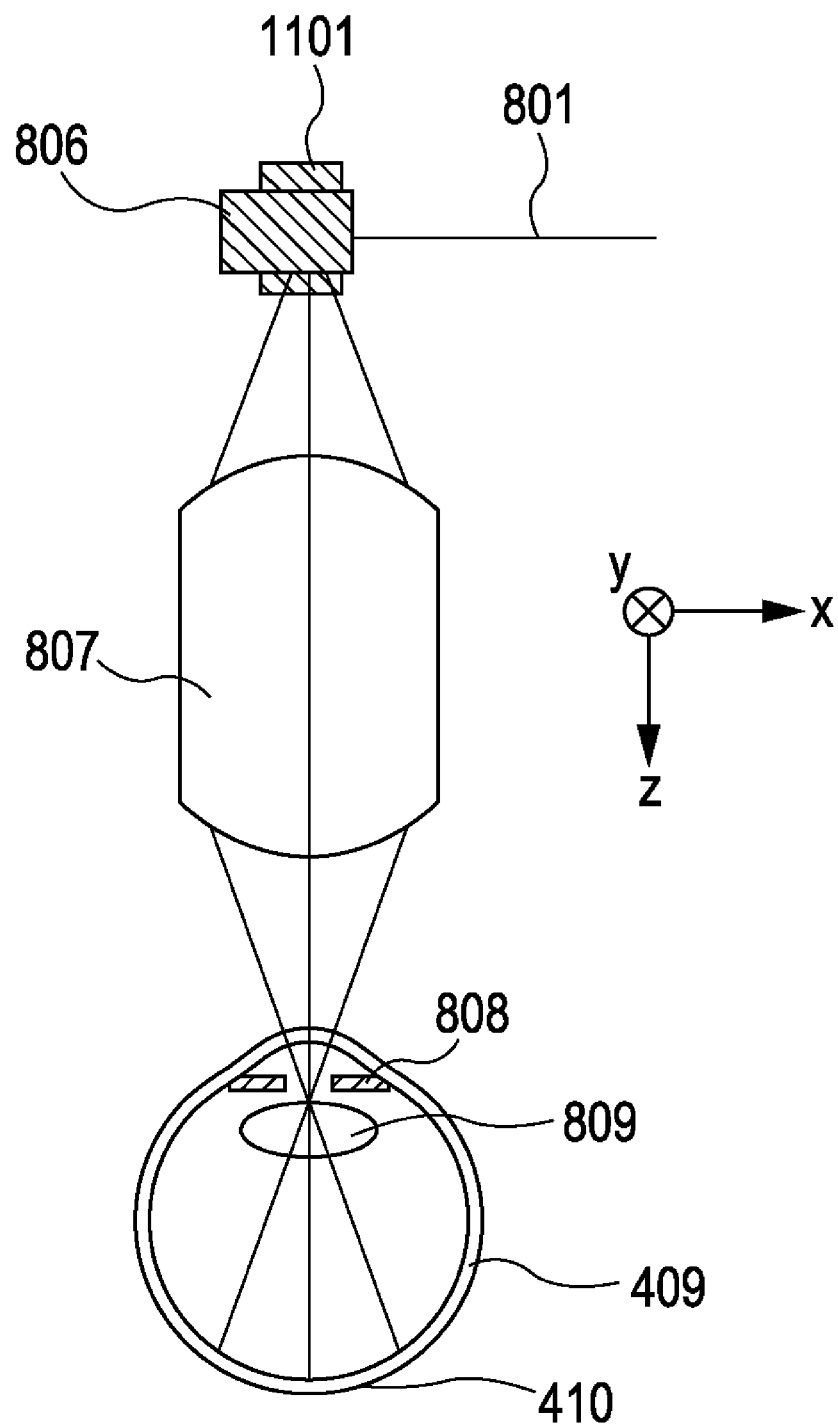

Moreover, referring to FIG. 5G, the MEMS multi-resonant scanner 1101 of this embodiment and the galvano scanner 806 for sub scanning are disposed next to each other so as to form a two-dimensional scanning system with a slight conjugate relationship without the use of a relay optical system, thereby allowing for further size reduction.

FIG. 5G schematically illustrates the configuration of a scanning optical system of an optical coherence measuring apparatus according to the second embodiment of the present invention.

According to this embodiment, an OCT image acquisition apparatus capable of efficiently forming three-dimensional tomographic images with weighted areas of importance can be reduced in size and perform high-speed operation.

Third Embodiment

A third embodiment of the present invention will now be described.

Figure 2C:
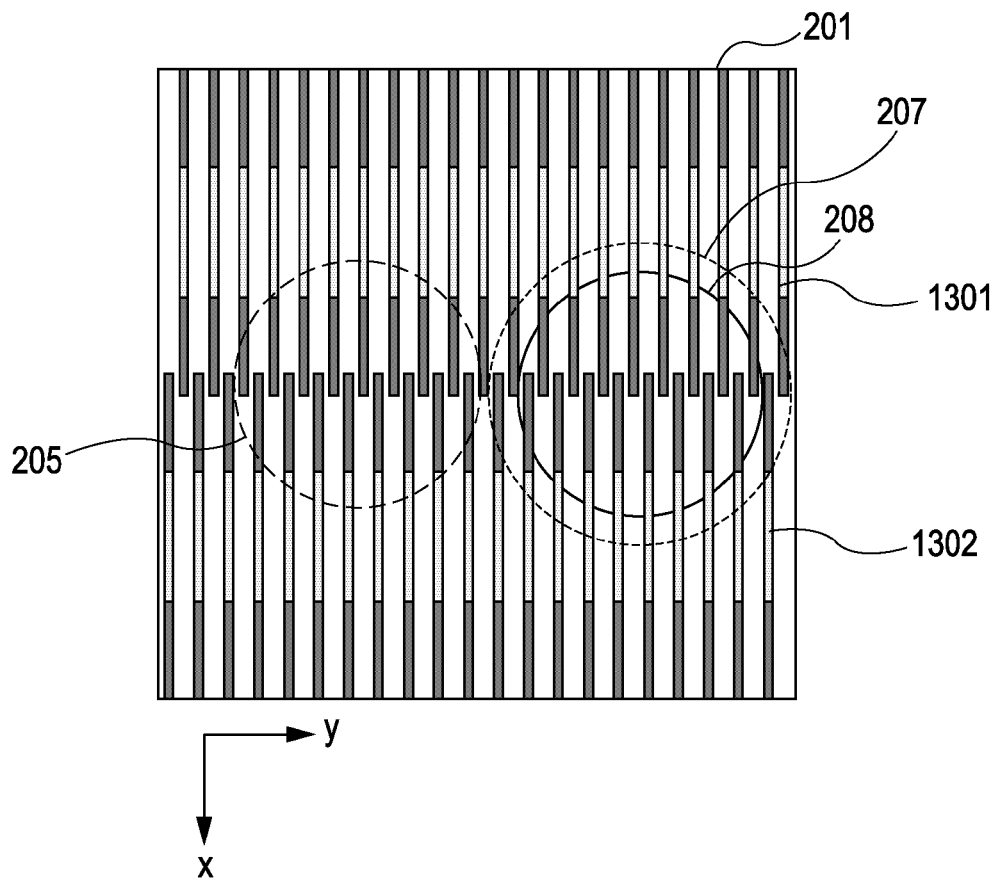
Figure 2D:
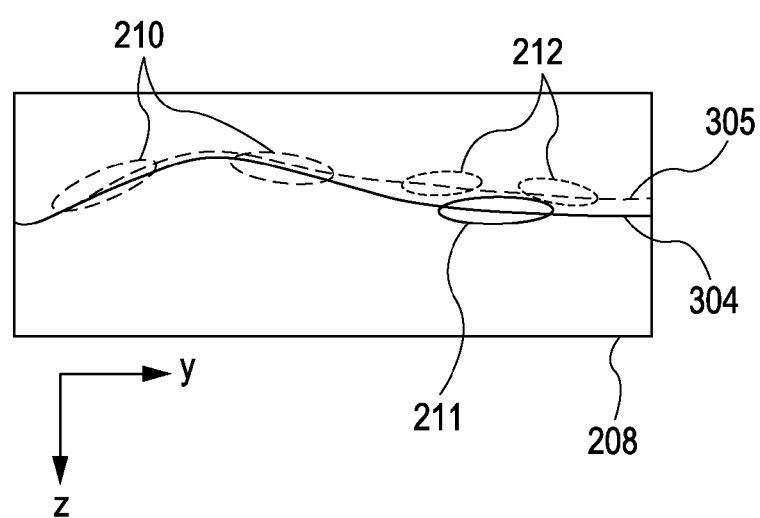

FIGS. 2C and 2D schematically illustrate how weighting control is performed on areas of importance in this embodiment. As shown in FIGS. 2C and 2D, the scan lines configured to scan the image acquisition region 201 in this embodiment are constituted by a first scan-line group 1301 and a second scan-line group 1302. Optical coherence tomographic images are acquired using these scan lines.

An OCT image acquisition apparatus using the first scan-line group 1301 and the second scan-line group 1302 will now be described.

Figure 3B:
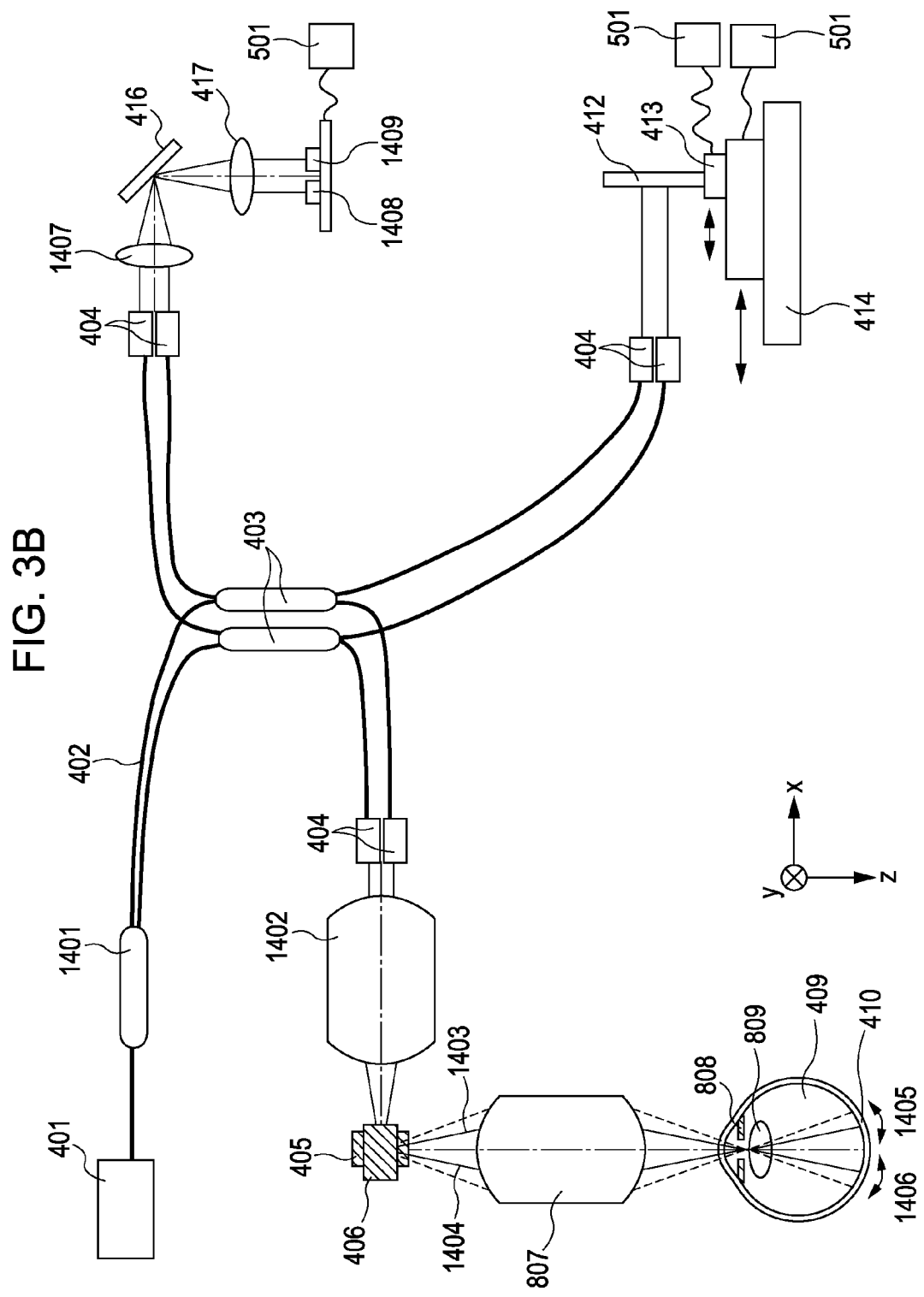

FIG. 3B schematically illustrates the configuration of an optical measuring system of an optical coherence measuring apparatus according to this embodiment. Light emitted from a light source 401 is sent to a fiber optical coupler 1401 via a single-mode optical fiber and is then equally transmitted to two optical fibers 402 by a distribution effect.

The two light beams are then distributed respectively to a signal light path and a reference light path by fiber optical couplers 403.

In the signal light path, two collimator lenses 404 are disposed in parallel to each other so that the signal light is emitted as two collimated beams. The two beams are made to meet each other substantially at the rotational center of reflective scanning of an x-axis scanner 405 by an imaging optical system 1402.

Subsequently, two signal light beams 1403 and 1404 travelling with a predetermined divergent angle therebetween via a y-axis scanner 406 enter the human eye 409 via an ocular optical system 807.

The two signal light beams 1403 and 1404 receiving an optical effect of the eye are simultaneously focused onto different positions of the fundus. In addition, by rotational scanning of the x-axis scanner 405 and the y-axis scanner 406, the two signal light beams 1403 and 1404 are two-dimensionally scanned in synchronization with each other over respective scanning ranges 1405 and 1406 while the two beams 1403 and 1404 are separated from each other by a predetermined distance on the fundus.

These two scanning processes are performed by the first scan-line group 1301 and the second scan-line group 1302 shown in FIGS. 2C and 2D.

On the other hand, reference light emitted as two collimated beams by collimator lenses 404 disposed in parallel to each other is reflected by a reference-light mirror 412 disposed on an optical delay-position high-speed fine driving device 413 and an optical delay-position global low-speed driving device 414 so that the light travels reversely through the light path.

The position of the reference-light mirror 412 is globally adjusted and controlled by controlling the optical delay-position global low-speed driving device 414 and the optical delay-position high-speed fine driving device 413.

Moreover, the position of the reference-light mirror 412 is finely adjusted and controlled so that the total light-path length of the reference light path is globally and finely adjusted to a predetermined length relative to the length of the signal light path.

The two signal light beams and the two reference light beams return to the fiber optical couplers 403 and are divided into light returning towards the light source 401 and light traveling towards an optical receiving system. However, since the signal light and the reference light are transmitted in the same basic mode in each light path, the light beams are combined and create coherent light.

The coherent light beams emitted as two collimated beams by parallel-arranged collimator lenses 404 are made to meet each other on a diffraction grating 416 by an imaging lens 1407.

In FIG. 3B, the diffraction grating 416 has a grating pattern arranged in a direction orthogonal to the plane of drawing. The diffraction grating 416 causes first-order diffraction light of each of the two coherent light beams to be wavelength-resolved in the direction orthogonal to the plane of drawing. The two light components create light intensity patterns on the respective line sensors 1408 and 1409 in accordance with spectral light intensities.

The line sensors 1408 and 1409 each include a plurality of pixels arranged one-dimensionally in the direction orthogonal to the plane of drawing in FIG. 3B.

Spectral optical-interference signals detected by the line sensors 1408 and 1409 undergo inverse Fourier transform processing by a control/signal-processing unit 501 and are subsequently formed into images. The images are combined together in accordance with scan positions so as to constitute the entire image acquisition region 201.

The configuration of the OCT image acquisition apparatus described above allows for parallel image acquisition by the first and second scan-line groups shown in FIGS. 2C and 2D.

Weighting to be given to the selected important areas 205, 206, and 207 in FIG. 2C by scan control in this embodiment will now be described. FIG. 2C schematically illustrates how scanning is performed in this embodiment. FIGS. 7C and 7D schematically illustrate how weighting is performed by scan control in this embodiment.

FIG. 7C is a graph showing an integration time Tp per pixel, a scan rate V, and a scan position x with respect to a scan time t and a scan position x. FIG. 7D illustrates how a scan operation is performed, including outward and homeward processes as well as the scan position x. Although FIG. 7D is basically the same as FIG. 2C, the orientation thereof is rotated by 90° relative to that of FIG. 2C.

In FIG. 7C, the x position is from x=0 to X in the outward scanning process and from x=X back to 0 in the homeward scanning process. In this embodiment, since the scanning operation is performed by using the first scan-line group and the second scan-line group both for the outward scanning process and the homeward scanning process, the first scan-line group is used for scanning substantially from 0 to X/2 and the second scan-line group is used for scanning substantially from X/2 to X. Thus, the scan position x is driven as a function x(t) of time t, as shown in the lowermost section of FIG. 7C. Regarding the use of these two scan-line groups, the first scan-line group is denoted by a solid line, whereas the second scan-line group is denoted by a dotted line in FIGS. 7C and 7D. In this embodiment, scanning is performed in a resonant fashion in order to achieve high speed, and therefore, the scan rate decreases according to a trigonometric function in the central area of a screen both for the first and second scan-line groups. By performing scanning in this manner, the rate V on a scan line reflects weighting information as a function V(x) of scan position x, as shown in the midsection of FIG. 7C.

In consequence, as a function Tp(x) of scan position x, the integration time Tp per pixel is made to increase in the midsection of a scan line, which is in an area of importance. In this embodiment, when the scan position x in the outward scanning process and the homeward scanning process is near X/2, the integration time Tp per pixel is three times or more.

In an area where the integration time Tp per pixel is increased, the optical interference signal increases and the S/N ratio thus rises.

The reason for this is, since a normal OCT operation area is where shot noise and thermal noise are limited, the S/N ratio is substantially proportional to the integration time.

Other Embodiments

The present invention is not specifically limited to the detailed configuration described in the first to third embodiments.

It is to be noted that, in configurations other than the above, partial modifications are permissible to an extent that they do not depart from the scope of the invention.

Figure 2E:
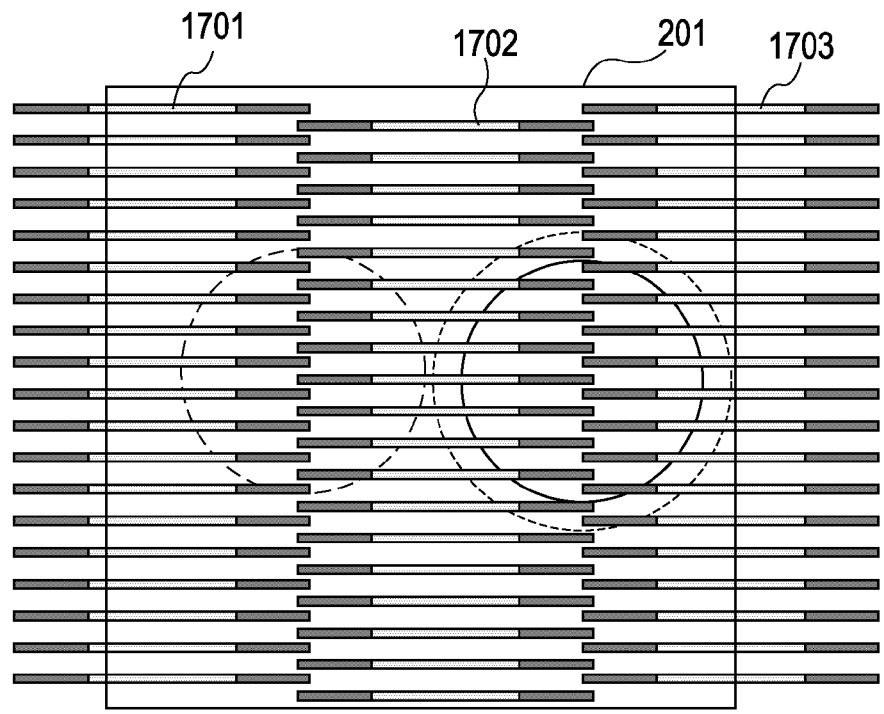
Figure 2E:
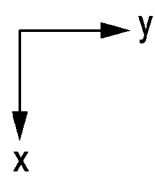
Figure 2F:
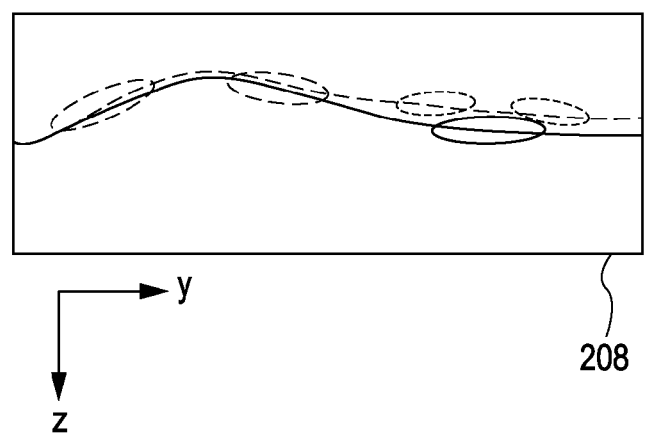

For example, in the parallel scanning system of the third embodiment, main scanning may be performed in the y-axis direction and weighting can be performed on two areas of importance in the y-axis direction by using three scan-line groups 1701, 1702, and 1703 so as to enhance the sensitivity of these areas, as shown in FIGS. 2E and 2F. The state of the scan lines in that case is shown in FIG. 2E.

Figure 6C:
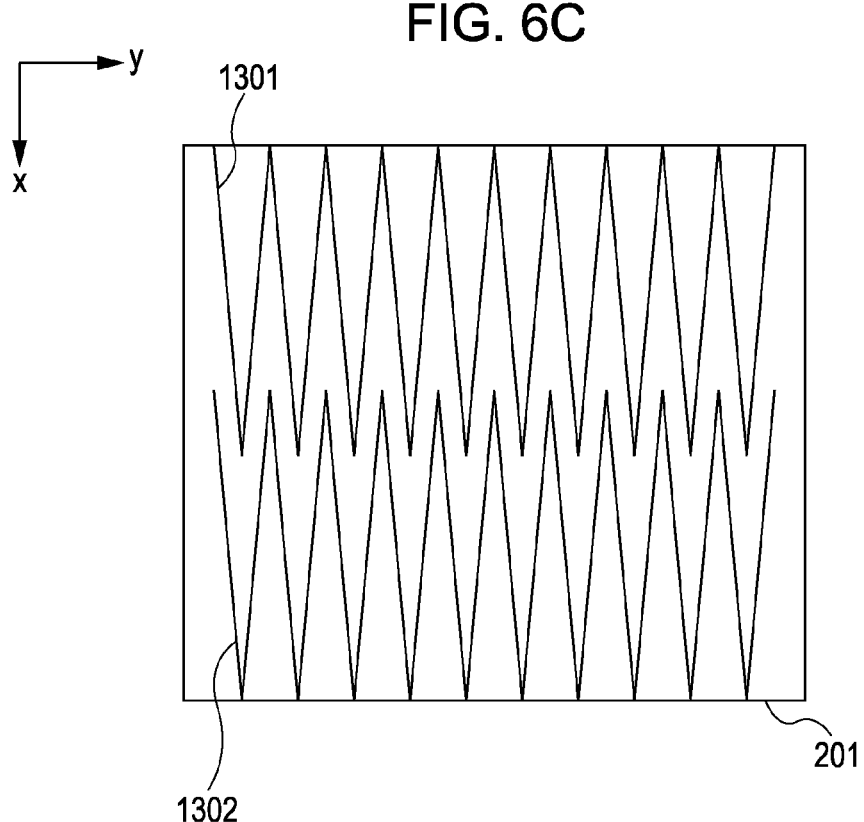
Figure 6D:
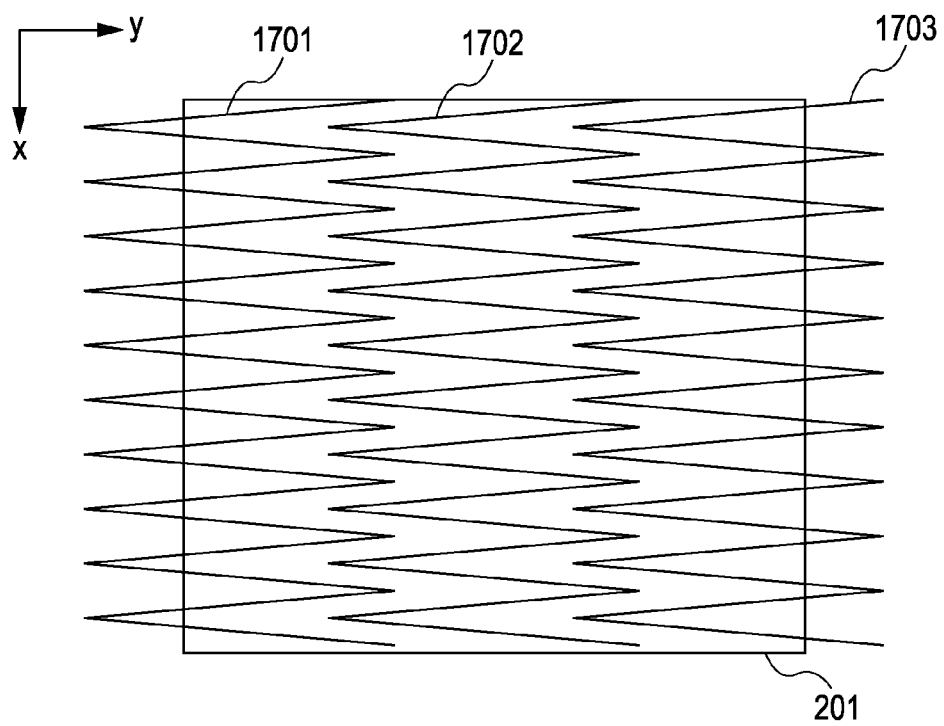

Referring to FIG. 2E, when two-dimensional scanning is to be performed at high speed, the scanning operation may actually be performed in a mode as schematically shown in FIGS. 6C and 6D in which sub scanning is performed in a continuous manner instead of a stepwise manner. Reference numerals 1301, 1302, 1701, 1702, and 1703 denote scan lines.

Figure 9B:
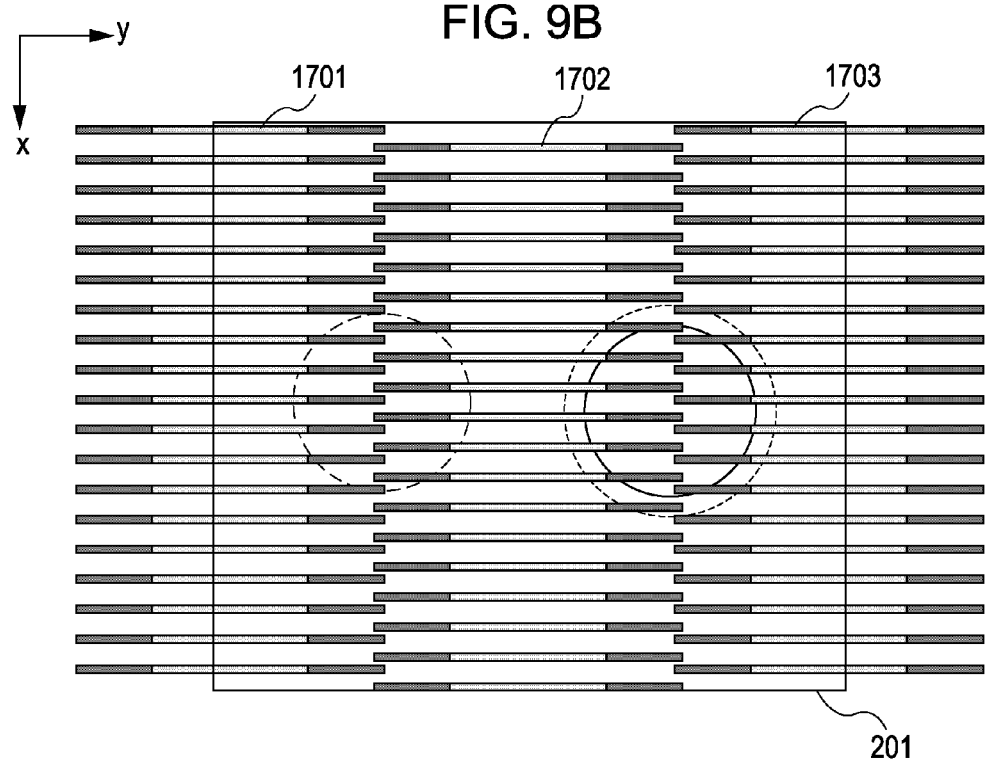
Figure 9C:
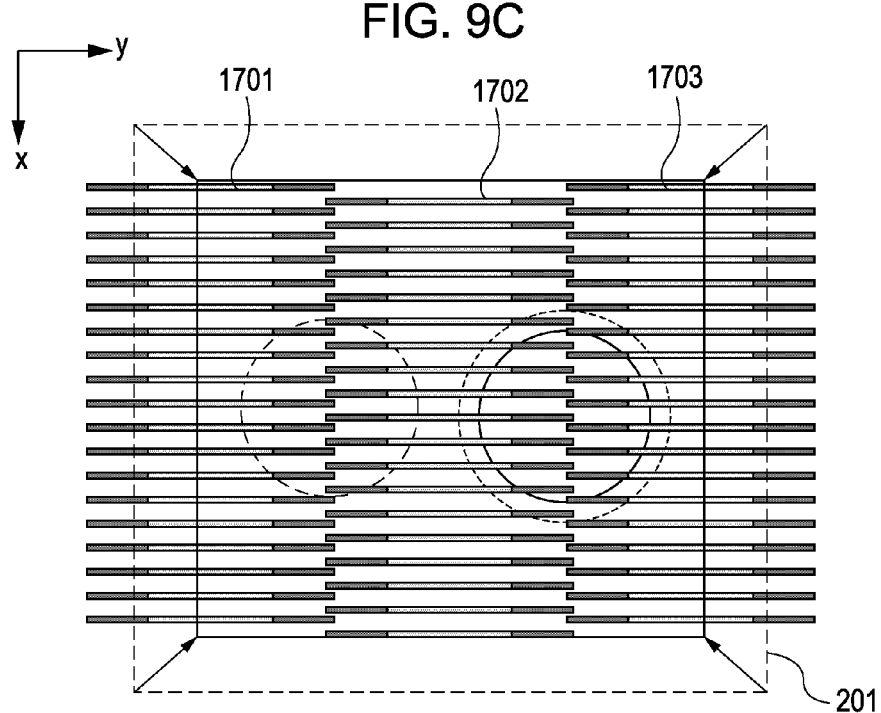

As another example of a modification, it is preferable to include an optical position adjustment unit configured to relatively change the scanning operation performed on an area given weighting information in accordance with the weighting information. Specifically, the optical system 1402 may be provided with a zoom function. For example, as shown in FIG. 9A, a zoom optical system 1408 equipped in the optical system 1402 is capable of changing the scan range of three beams output from collimator lenses 404, that is, changing the distance between scan centers of the beams. Accordingly, by performing zooming from the scan range of the scan-line group 1703 in FIG. 9B to the scan range of the scan-line group 1703 in FIG. 9C, joint positions between multiple beams can be appropriately adjusted to joint locations, that is, locations where the image quality is to be enhanced by weighting, even if the distance between a macula and an optic disk varies among examined subjects. In consequence, the advantages of the present invention can be achieved with respect to various subjects.

Figure 3C:
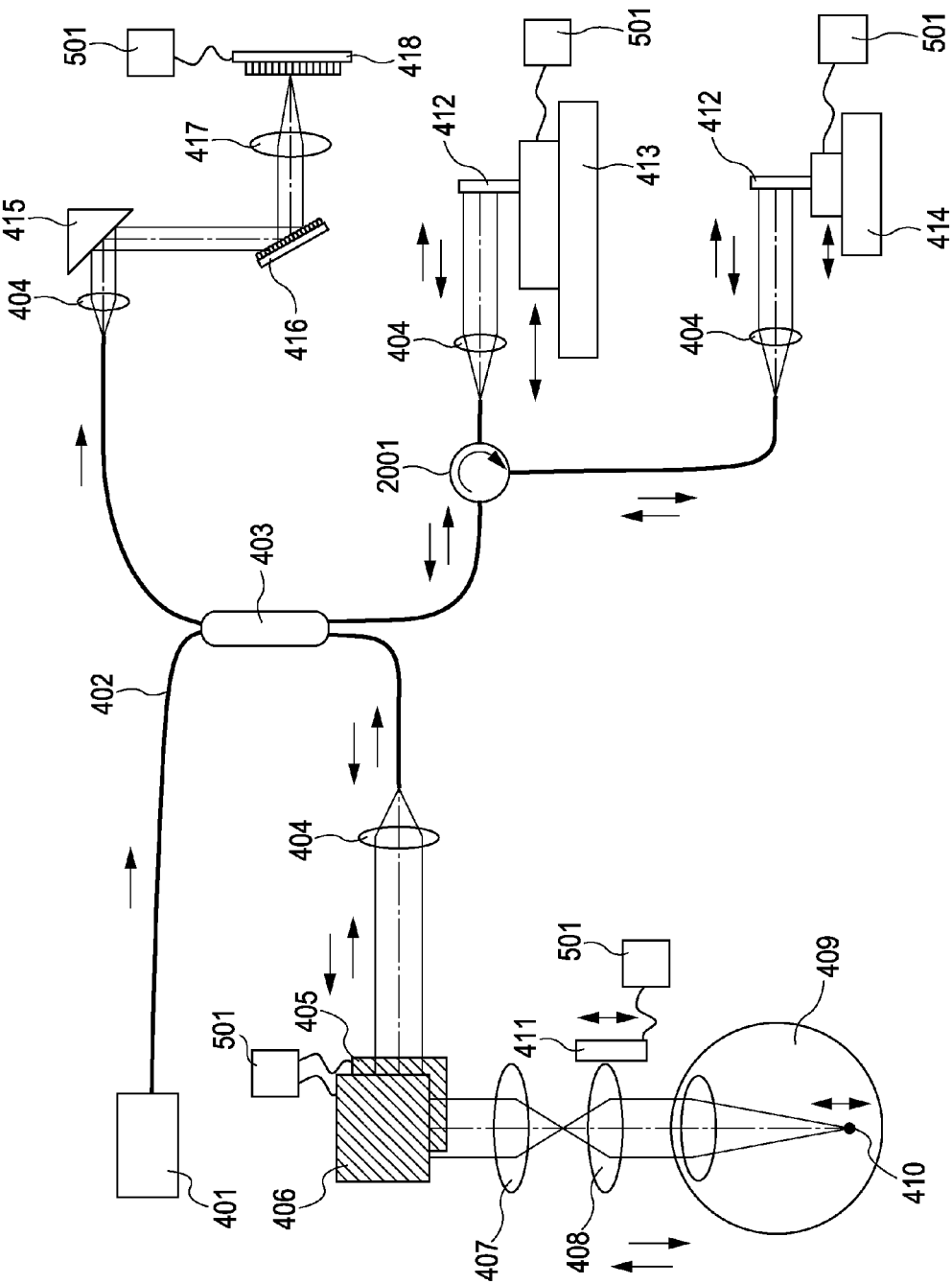

Furthermore, the optical delay driving devices may be defined, for example, by those shown in FIG. 3C.

Figure 8A:
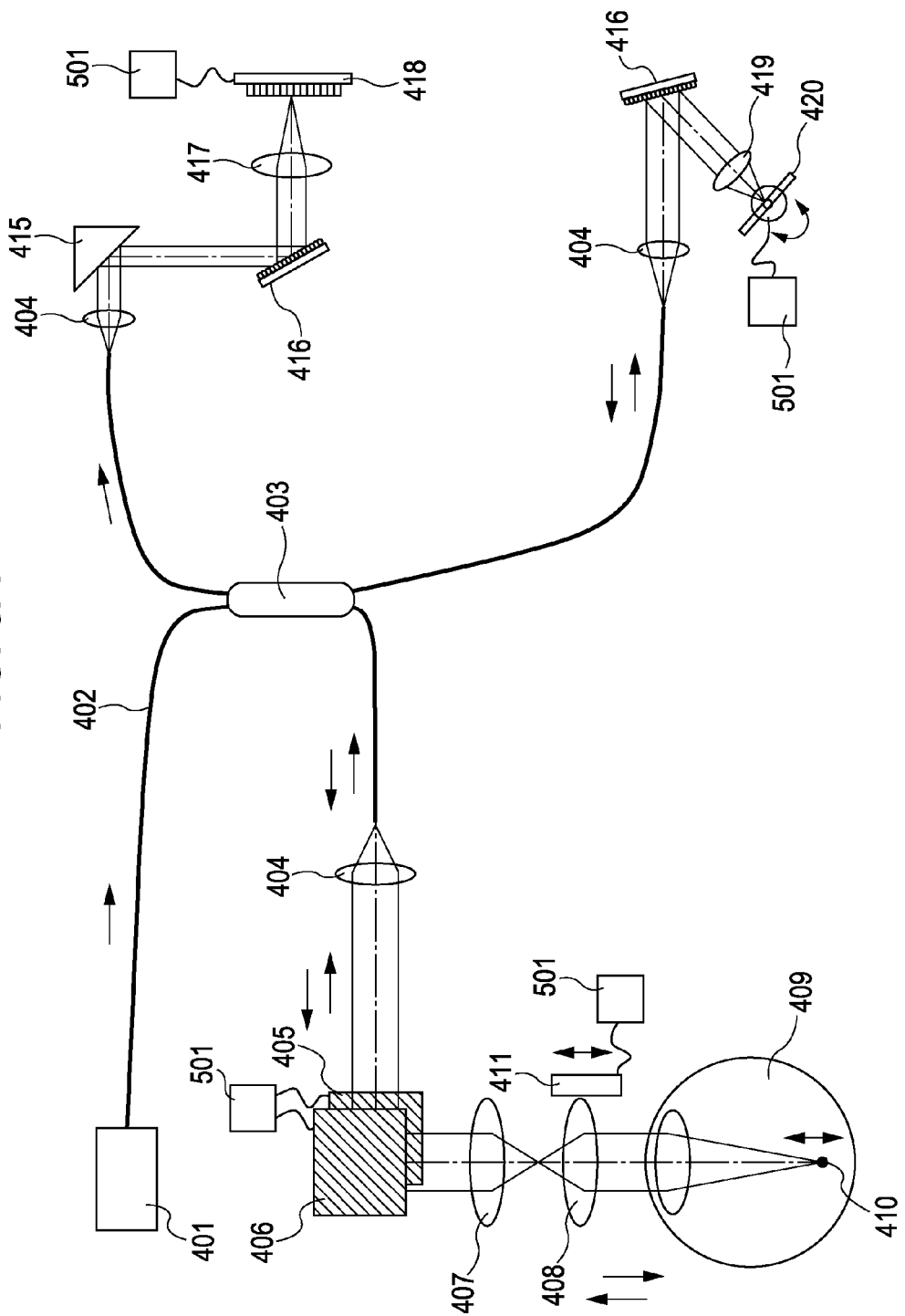
FIGS. 8A and 8B schematically illustrate an optical measuring system according to an embodiment of the present invention and FIG. 8C schematically illustrates an optical measuring system of related art.

Specifically, the optical delay-position high-speed fine driving device 413 and the optical delay-position global low-speed driving device 414 may be disposed separately as different reference-light mirrors and arranged in series in the reference light path by using an optical coupler such as an optical circulator 2001. As another modification, for example, a rapid scanning optical delay (RSOD) system shown in FIG. 8A may be used. Specifically, this optical delay system is formed by adding a linear phase difference to the optical frequency of light wavelength-resolved by the diffraction grating 416. Phase difference adjustment in this case is performed by controlling the angle of a rotational reflective mirror 420 that receives light traveling through a lens 419.

When the aforementioned RSOD system is used, it is preferable that the delay length that varies among individuals be set as an offset angle and that angular control for zero-delay position adjustment of weighting be performed dynamically based on the offset angle.

Figure 6E:
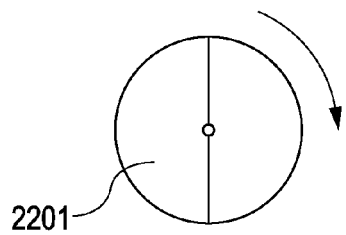
Figure 6F:
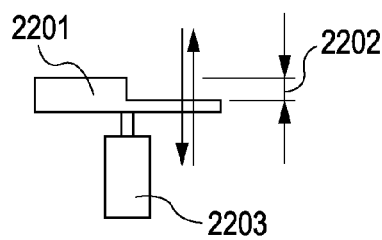
Figure 8B:
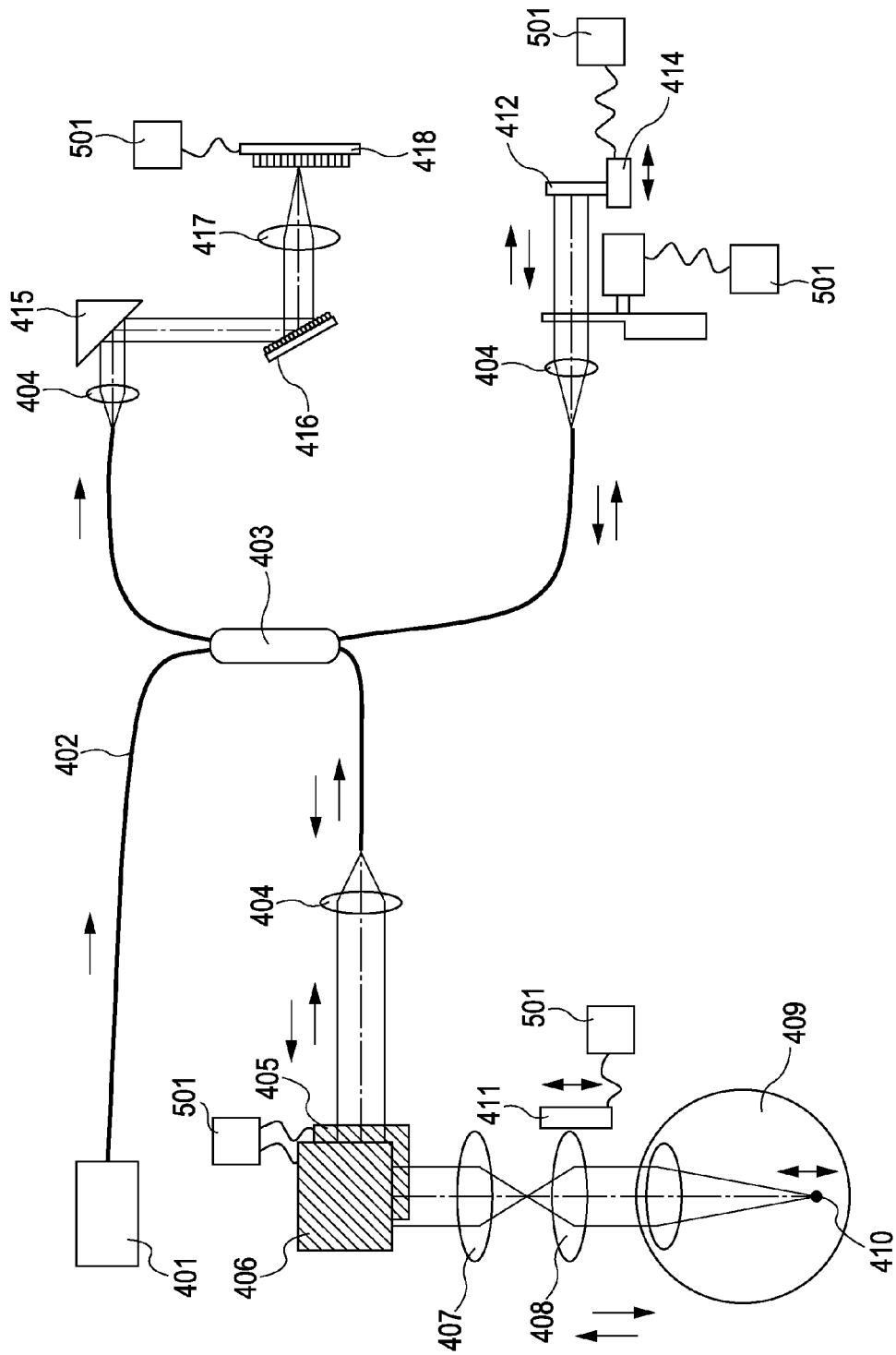

As another modification, for example, as a zero-delay-position adjustment unit for weighting, a transparent rotatable disk body 2201 may be incorporated as a transmissive element in the reference light path, as shown in FIGS. 8B, 6E and 6F.

In this case, the rotatable disk body 2201 is provided with a predetermined step 2202 and is configured to periodically modulate the reference light path by rotating.

The rotational speed of a motor 2203 is adjustably controlled so as to be in synchronization with the repeating rate of main scanning. Therefore, a zero-delay position is periodically modulated in accordance with a main scanning position.

Figure 6G:
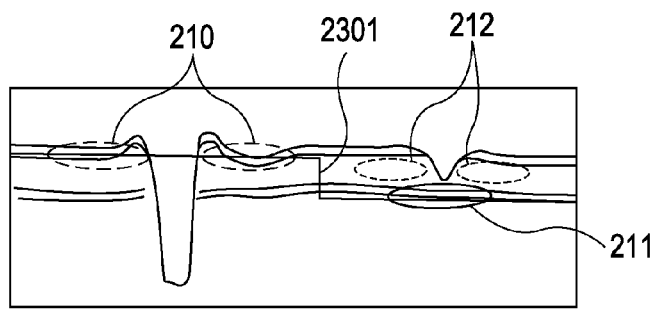
Figure 6H:
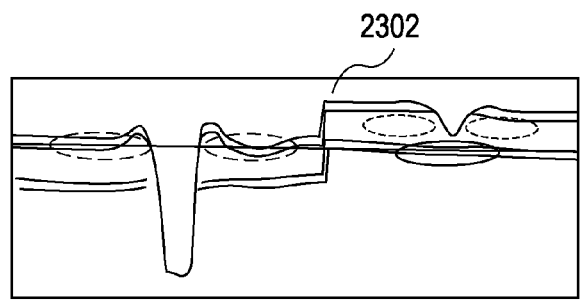
Figure 6I:
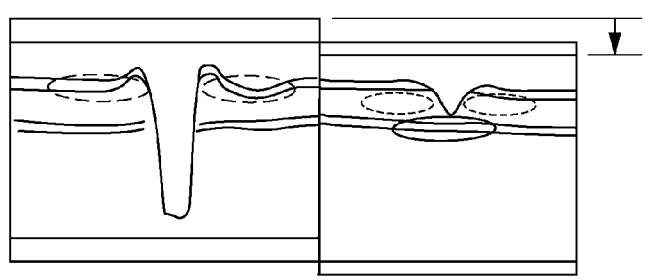

FIGS. 6G, 6H, and 6I schematically illustrate how weighted image correction is performed in this case.

FIG. 6G illustrates the positional relationship between a fundus tomographic layer and a zero-delay position 2301. The zero-delay position 2301 changes in a binary fashion between an optic disk and a macula.

In this case, if a tomographic image is formed without any correction, a delay position is formed linearly within a screen. This results in a discontinuous displacement 2302 added to the weighted tomographic image itself, as shown in FIG. 6H.

Therefore, as preferred weighted image correction, light-path-length difference information to be added to the rotatable disk body 2201 is added thereto during image formation so that a continuous tomographic image as shown in FIG. 6I can be formed again.

Such weighted image correction may be performed automatically or may be performed semi-automatically or manually by a user.

Although the integration time per pixel is made to increase in the above embodiments, the number of pixels per unit scan-line length, for example, may be made to increase instead of increasing the integration time. In that case, the transverse resolution is subject to weighting.

Furthermore, regarding the system having two resonance frequencies in the second embodiment, for example, a system having three or more resonance frequencies may be used as an alternative.

Moreover, by appropriately adjusting, for example, the phase difference or the amplitude ratio between the vibrators, combined scan control suitable for areas of importance can be performed.

In the above embodiments, although a zero-delay position can be set inside an examination object in the depth direction and a so-called full range complex method is used to remove mirror images by inverse Fourier transform processing, the present invention is not limited to this.

For example, the zero-delay position may be set in a vitreous body which is located in a shallower section than the fundus surface and where the signal level is low and a mirror image is effectively negligible. Moreover, in order to increase the sensitivity to the utmost level, the zero-delay position may be adjusted curvedly along the fundus surface or with a combination of approximate lines by using the zero-delay adjustment unit mentioned in the above embodiments.

Furthermore, for example, although weighting selection is performed by pre-scanning of a fundus monitor and by user input operation in the above embodiments, a standard fundus image template may be used as an alternative to image acquisition by pre-scanning.

Regarding important-area selection, automatic selection may be performed using standard preset values.

When pre-scanning is to be performed, an ophthalmologic measuring apparatus different from the OCT image acquisition apparatus according to the present invention, such as a fundus camera, an axial-length measuring unit, or the like combined with an OCT device, can be used.

Based on measurement information obtained by a measuring apparatus of a type other than an OCT type, the standard fundus image template may be displayed after enlarging or reducing it and performing conversion adjustment, such as rotation, thereon. Based on the standard fundus image template, user selection may be performed or automatic selection may be performed by applying preset values thereto.

Figure 10A:
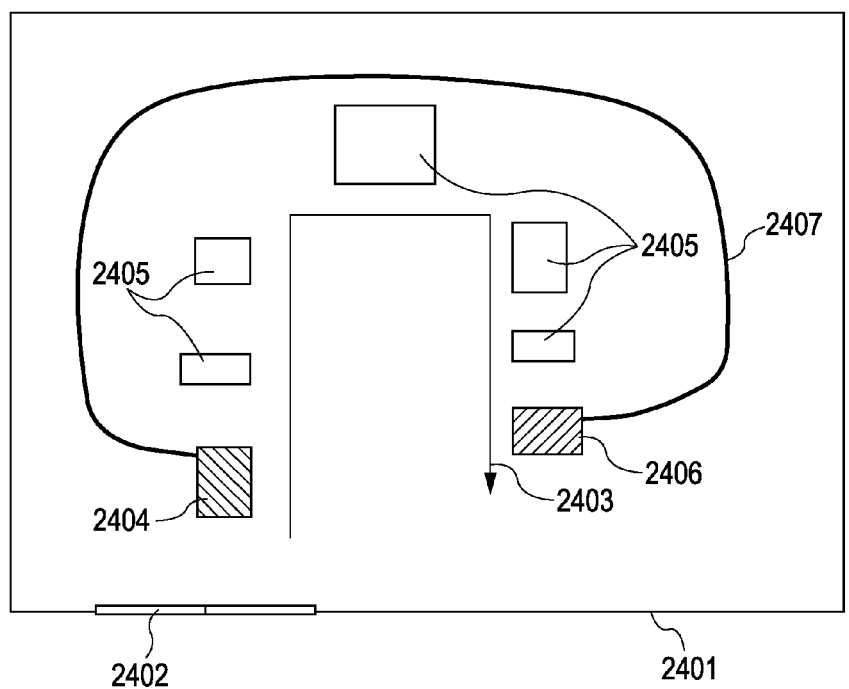
FIG. 10A is a schematic diagram for explaining an image acquisition apparatus according to an embodiment of the present invention and FIGS. 10B and 10C are schematic diagrams for explaining an image acquisition apparatus of related art.

In group examinations in particular, an ophthalmologic measuring apparatus 2404 is disposed in an earlier part of an examination route 2407, as schematically shown in FIG. 10A, whereas an OCT image acquisition apparatus 2406 according to the present invention is disposed in a latter part of the examination route 2407.

After the measurement performed by the ophthalmologic measuring apparatus 2404, the information may be transferred via a network to the apparatus 2406 according to the present invention during examination by other examination measuring apparatuses 2405. Selection of areas of importance may be completed before examined subjects are actually examined so that the total examination time can be shortened.

Although the high-resolution OCT optical-coherence measuring apparatus according to the present invention is particularly suitable for ophthalmologic screening in group examinations, the apparatus can be used as other various kinds of diagnostic apparatuses and examination apparatuses for biological observation, such as dermal observation or endoscopic observation, industrial quality control, and the like.

The present invention can also be achieved by performing the following process. Specifically, a software program that carries out the functions of the above embodiments may be supplied to a system or an apparatus via a network or various kinds of storage media, and a computer (or a CPU, an MPU, or the like) of the system or the apparatus may read out and execute the program.

COMPARISON EXAMPLE

Common FD-OCT will now be described.

Figure 8C:
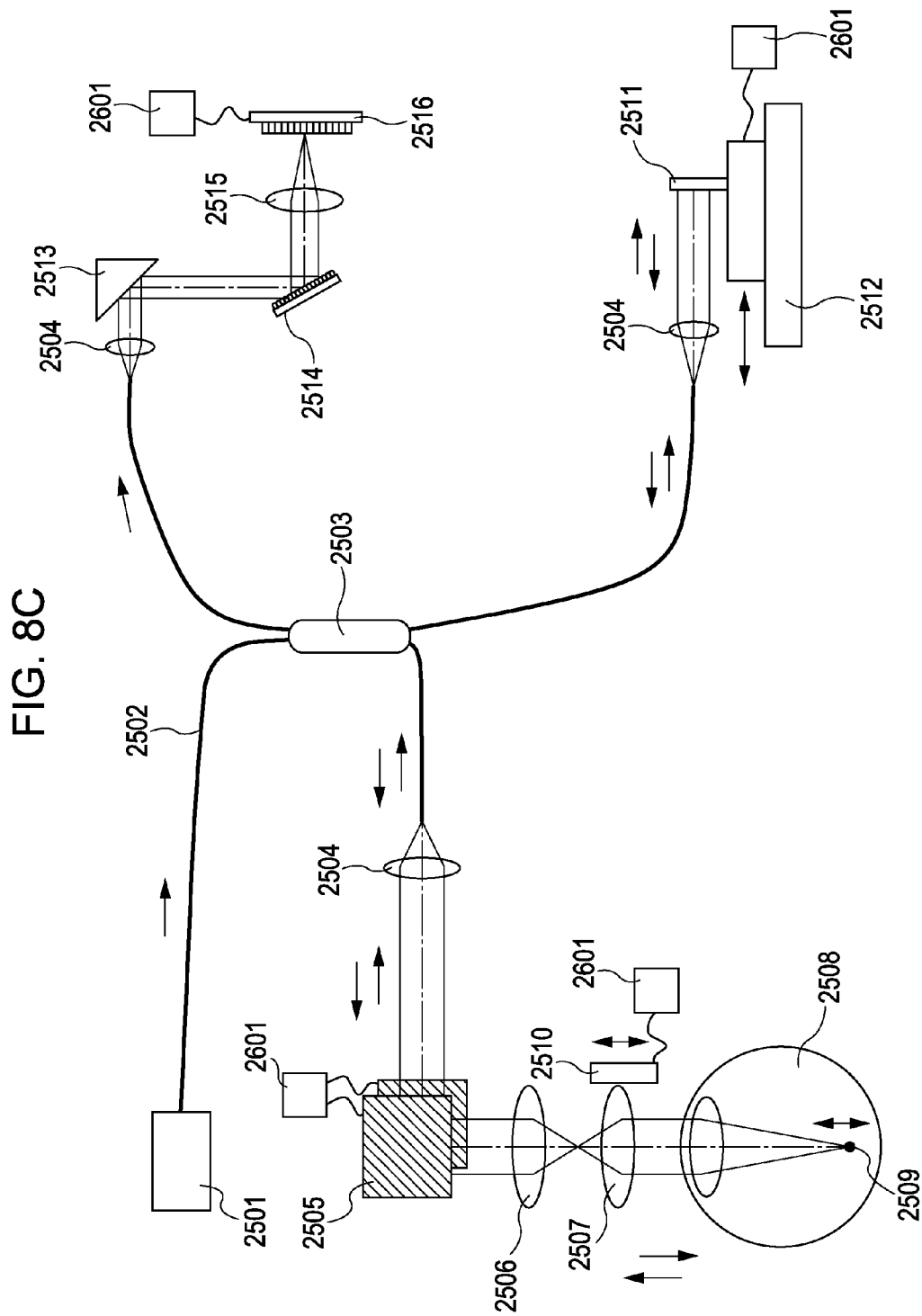

FIG. 8C schematically illustrates a typical ophthalmologic FD-OCT apparatus of the related art. Specifically, light emitted from a light source 2501 is optically guided by a single-mode optical fiber 2502 so as to enter a fiber optical coupler 2503. The fiber optical coupler 2503 is a so-called 2×2 type and distributes the light received through the fiber 2502 to two output fibers. One of the output fibers is connected to a human-fundus image acquisition optical system acting as a signal light path of a Michelson interferometer, whereas the other output fiber is connected to a reference light path of an interferometer. In the signal light path, the light emitted from the fiber terminal is converted to collimated light by a collimator lens 2504 and then propagates through space so as to enter an x-axis/y-axis scanner 2505. The x-axis/y-axis scanner 2505 is a reflective optical scanning device that performs two-dimensional reflective angle control. The reflected signal light is optically guided by a scan lens 2506 and an ocular lens 2507 so as to enter a human eye 2508. Through the scanning optical system constituted by the x-axis/y-axis scanner 2505, the scan lens 2506, and the ocular lens 2507, the signal light, which is collimated light and receiving an optical effect of the eye, is focused onto a fundus observation area 2509 and is two-dimensionally scanned over a surface on the fundus substantially orthogonal to the light axis. The ocular lens 2507 adjusts the focus position in the depth direction. The scan control and the focus control are collectively performed together with other control by a control/signal-processing unit 2601 connected to the x-axis/y-axis scanner 2505 and a focus drive actuator 2510. Of the reflected light and rearward diffused light from the fundus observation area 2509, the signal light passing through substantially the same light path and travelling in the reverse direction returns to the fiber optical coupler 2503 via the collimator lens 2504. On the other hand, the reference light is split by the fiber optical coupler 2503. The reference light is then converted to collimated light by a collimator lens 2504 and is reflected by a reference-light mirror 2511 disposed on an optical delay driving device 2512 so that the light travels reversely through the light path. The position of the reference-light mirror 2511 is controlled by controlling the optical delay driving device 2512 so that the total light-path length of the reference light path is adjusted to a predetermined length on the basis of the length of the signal light path, particularly including compensation for different axial lengths among individuals. The reference-light mirror 2511 is connected to the control/signal-processing unit 2601 and is collectively controlled together with other control. The reversely-travelling reference light returns to the fiber optical coupler 2503 via the collimator lens 2504.

Although the signal light and the reference light returning to the fiber optical coupler 2503 are each split into a component that returns to the light source 2501 and a component that travels toward a coherent-light receiving system, the signal light and the reference light propagate through the same single-mode fiber, meaning that they are combined and create optical coherence.

The coherent-light receiving system is a spectroscope in this example, and therefore, OCT in this example is spectral domain OCT (SD-OCT) in which spectral coherence is measured. The coherent light is converted to collimated light by a collimator lens 2504 and is guided to a diffraction grating 2514 by a reflective mirror 2513. Due to the effect of the diffraction grating 2514, the light travels at different angles in accordance with wavelength components of the light including first-order diffraction light. The wavelength components of the coherent light entering an imaging lens 2515 at different angles form images at different positions on a line sensor 2516 in accordance with their respective angles. The image of each wavelength component is read as a light intensity in accordance with each pixel of the line sensor 2516, and a signal is sent to the control/signal-processing unit 2601.

The configuration of the control/signal-processing unit 2601 of the related art will be described in detail with reference to FIG. 4B. The control/signal-processing unit 2601 is configured to control the x-axis/y-axis scanner 2505, the optical delay driving device 2512, the focus drive actuator 2510, and the line sensor 2516. On the other hand, the control/signal-processing unit 2601 is equipped with drivers and a receiver that are configured to receive angle detection signals, position detection signals, and optical-signal detection signals. Specifically, a line image receiver 2607 receives a group of light intensity signals from the line sensor 2516, and an FFT processor 2608 performs inverse Fourier transform processing at high speed on the light intensity signal group. The resultant signal group is sent to a central processor 2603. The central processor 2603 receives digital optical-interference signals, having undergone inverse Fourier transform processing, in a time-series fashion and compares each signal with a scanner-position-signal/synchronization-signal from an x-axis/y-axis-scanner driver 2602, a delay-position-signal/synchronization-signal from an optical-delay-drive driver 2605, and a focus-position signal from a focus driver 2606 so as to match the relationships between the optical interference signals and the positions in the fundus observation area 2509. Subsequently, the optical interference signals are allocated to predetermined pixels and formed into images, which are then displayed on an image display 2604. Such FD-OCT allows for three-dimensional fundus measurement within an image acquisition time of about one to three seconds.

An OCT scanning method of the related art will also be described below.

Figure 7E:
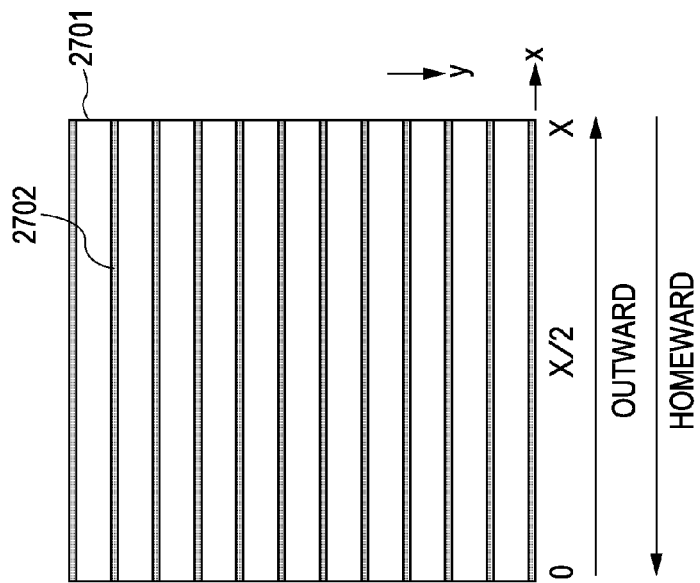
FIGS. 7A to 7D schematically illustrate how weighting is performed by scan control according to an embodiment of the present invention and FIGS. 7E and 7F schematically illustrate how weighting is performed by scan control in related art.
Figure 7F:
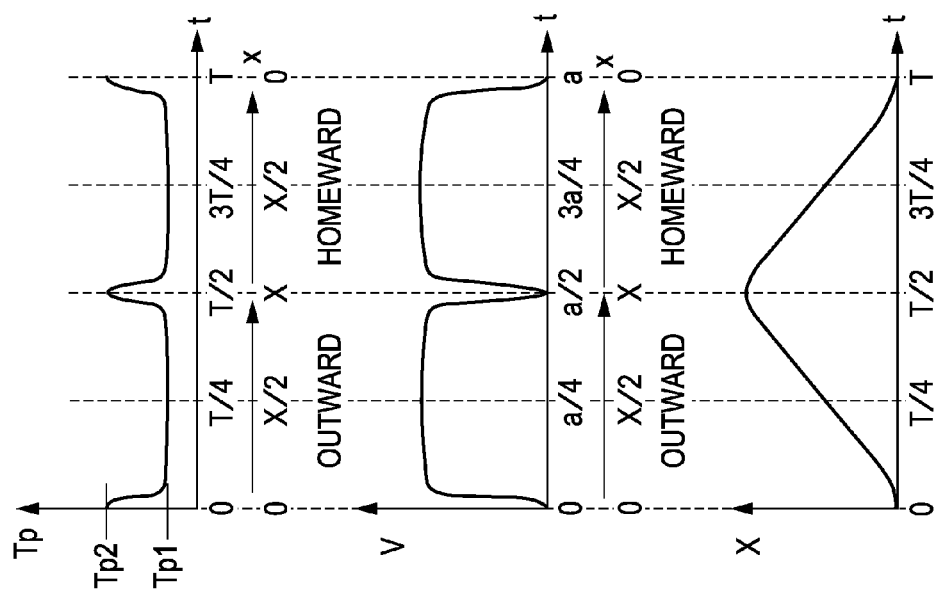

FIG. 7F schematically illustrates an example of how scanning is performed in the optical-coherence measuring apparatus of the related art. An OCT image acquisition region 2701 is a top view that schematically shows an image acquisition region in the horizontal direction of OCT. Two axes in the horizontal direction are an x axis and a y axis that have the directions shown in FIG. 7F. Each of scan lines 2702 schematically represents so-called main scanning in the OCT image acquisition region 2701. In this example of related art, the x-axis direction corresponds to the main scanning direction. With a plurality of scan lines arranged in the y-axis direction, two-dimensional scanning is performed. In OCT, pixels are one-dimensionally arranged in the scanning direction within each scan line. Optical tomographic information based on optical reflectance in a depth direction orthogonal to the plane of drawing (the depth direction will be referred to as "z-axis direction" hereinafter) is obtained for each of the pixels. In consequence, with such two-dimensional scanning, three-dimensional tomographic data is acquired.

An example of scan control in the image acquisition apparatus of the related art will now be described with reference to FIGS. 7E and 7F. FIG. 7E is a graph showing an integration time Tp per pixel, a scan rate V, and a scan position x with respect to a scan time t and a scan position x. On the other hand, FIG. 7F illustrates how a scan operation is performed, including outward and homeward processes as well as the scan position x. Reference character T in FIG. 7E denotes the total time for the outward and homeward scanning processes, that is, one cycle of main scanning operation. The outward scanning process is from t=0 to T/2, whereas the homeward scanning process is from T/2 to T. The x position is from x=0 to X in the outward scanning process and from x=X back to 0 in the homeward scanning process. In this example, the scan position x is controlled in a triangular-wave manner as much as possible as a function x(t) of time t. In other words, the scan rate V on a scan line is controlled as stably or uniformly as possible as a function V(x) of scan position x for the purpose of achieving a uniform image quality. In consequence, the integration time Tp per pixel is made as constant as possible as a function Tp(x) of scan position x.

Figure 10B:
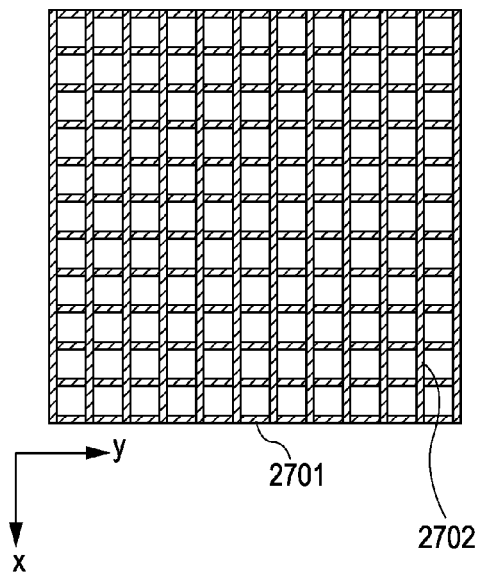
Figure 10C:
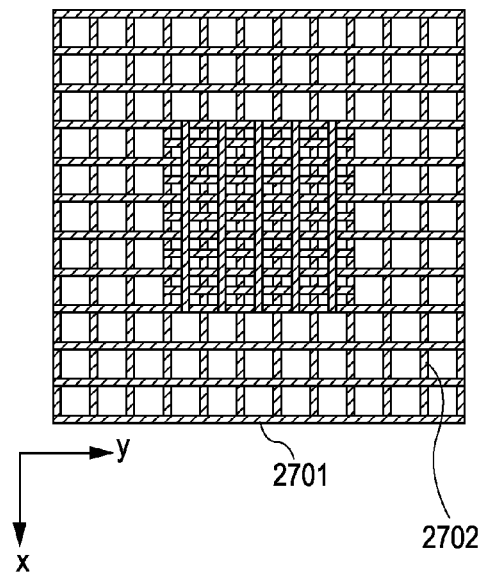

However, in general three-dimensional OCT acquisition, that is, two-dimensional scanning, pixels are densely arranged on each scan line, whereas the distance between pixels, that is, the distance between scan lines, is not dense in the sub scanning direction orthogonal to the scan lines. To adjust this, the scan lines are sometimes arranged on a grating as shown in FIG. 10B by switching the main scanning direction and the sub scanning direction. FIG. 10B schematically illustrates an example of a scan-line configuration in an optical coherence measuring apparatus of the related art.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An image acquisition apparatus comprising:
    a scanning unit configured to scan a plurality of signal lights in an object;
    a control unit configured to control the scanning unit such that, among scanning regions of the plurality of signal lights in the object, parts of adjacent scanning regions are overlapped with each other at a predetermined portion of the object; and
    an acquiring unit configured to acquire at least a tomographic image of the object based on a plurality of lights obtained by combining each of a plurality of return lights from the object irradiated with the plurality of signal lights and each of a plurality of reference lights corresponding to each of the plurality of signal lights.

2. The image acquisition apparatus according to claim 1, further comprising a display control unit configured to cause a display unit to display the tomographic image,
    wherein the object is a fundus of an eye to be examined,
    wherein the predetermined portion is at least one of a macula and an optic disk of the fundus, and
    wherein the display control unit causes the display unit to display an image of the fundus of the eye to be examined.

3. The image acquisition apparatus according to claim 2, further comprising a portion designating unit configured to designate, as the predetermined portion, at least one of the macula and the optic disk of the fundus on the image of the fundus of the eye to be examined, wherein the control unit controls the scanning unit such that the parts of the adjacent scanning regions are overlapped with each other at the designated portion, and wherein the display control unit causes the display unit to display the image of the fundus of the eye by overlapping a display form representing the scanning regions in accordance with the designation by the portion designating unit.

4. The image acquisition apparatus according to claim 1, wherein the acquiring unit acquires an image by combining a plurality of tomographic images each corresponding to each of the plurality of lights based on the scanning regions.

5. An image acquisition apparatus comprising:
a scanning unit configured to scan a plurality of signal lights in an object;
a control unit configured to control the scanning unit such that, among scanning regions of the plurality of signal lights in the object, parts of adjacent scanning regions are overlapped with each other in a main-scanning direction of the scanning unit; and
an acquiring unit configured to acquire at least a tomographic image of the object based on a plurality of lights obtained by combining each of a plurality of return lights from the object irradiated with the plurality of signal lights and each of a plurality of reference lights corresponding to each of the plurality of signal lights.

6. The image acquisition apparatus according to claim 5, further comprising a display control unit configured to cause a display unit to display the tomographic image,
wherein the object is a fundus of an eye to be examined,
wherein the control unit controls the scanning unit such that a predetermined portion of the fundus is the overlapped region, and
wherein the display control unit causes the display unit to display an image of the fundus of the eye to be examined.

7. The image acquisition apparatus according to claim 6, further comprising a portion designating unit configured to designate at least one of a macula and an optic disk of the fundus as the predetermined portion on the image of the fundus of the eye to be examined,
wherein the control unit controls the scanning unit such that the parts of the adjacent scanning regions are overlapped with each other at the designated portion, and
wherein the display control unit causes the display unit to display the image of the fundus of the eye by being overlapped with a display form representing the scanning regions in accordance with the designation by the portion designating unit.

8. The image acquisition apparatus according to claim 5, wherein the acquiring unit acquires an image by combining a plurality of tomographic images each corresponding to each of the plurality of lights based on the scanning.

9. An image acquisition apparatus comprising:
a scanning unit configured to scan a signal light in an object;
a control unit configured to control the scanning unit such that a scanning speed of the scanning unit is lower at a predetermined portion of the object than at a portion other than the predetermined portion of the object; and
an acquiring unit configured to acquire at least a tomographic image of the object based on a light obtained by combining a return light from the object irradiated with the signal light and a reference light corresponding to the signal light.

10. The image acquisition apparatus according to claim 9, wherein the control unit lowers the scanning speed of the scanning unit in a main-scanning direction in the predetermined portion.

11. The image acquisition apparatus according to claim 9, further comprising a display control unit configured to cause a display unit to display the tomographic image,
wherein the object is a fundus of an eye to be examined,
wherein the predetermined portion is at least one of a macula and an optic disk of the fundus, and
wherein the display control unit causes the display unit to display an image of the fundus of the eye to be examined.

12. The image acquisition apparatus according to claim 11, further comprising a portion designating unit configured to designate at least one of the macula and the optic disk of the fundus as the predetermined portion on the image of the fundus of the eye to be examined,
wherein the control unit lowers the scanning speed at the designated portion, and
wherein the display control unit causes the display unit to display the image of the fundus of the eye by being overlapped with a display form representing the scanning regions in accordance with the designation by the portion designating unit.

13. The image acquisition apparatus according to claim 12, wherein the portion designating unit designates a disease, and designates a portion corresponding to the disease in response to the designation of the disease.

14. The image acquisition apparatus according to claim 11, further comprising a light-path length changing unit configured to change a difference in light-path length between a light-path length of the signal light and a light-path length of the reference light, wherein, in a case where the light-path length changing unit changes the difference in light-path length in the acquisition of a tomographic image of the macula and a tomographic image of the optic disk, the acquiring unit corrects a positional alteration in a depth direction corresponding to the change of the difference in light-path length to acquire the image by combining the plurality of tomographic images.

15. The image acquisition apparatus according to claim 9, wherein the acquiring unit removes a mirror image based on a position in a light path of the signal light corresponding to a light path of the reference light.

16. an image acquisition apparatus comprising:
a display control unit configured to cause a display unit to display an image of a fundus of an eye to be examined; and
a portion designating unit configured to designate at least one of a macula and an optic disk of an fundus of an eye to be examined on the image of the fundus of the eye to be examined,
wherein the display control unit causes the display unit to display the image of the fundus of the eye by being overlapped with a display form representing a position of the portion designated by the portion designating unit.

* * * * *